United States Patent
Loke et al.

(10) Patent No.: US 11,397,180 B2
(45) Date of Patent: Jul. 26, 2022

(54) METHODS AND COMPOSITIONS FOR RAPID FUNCTIONAL ANALYSIS OF GENE VARIANTS

(71) Applicant: ALBERT EINSTEIN COLLEGE OF MEDICINE, INC., Bronx, NY (US)

(72) Inventors: Johnny C. Loke, Nanuet, NY (US); Harry Ostrer, New York, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 430 days.

(21) Appl. No.: 15/819,221

(22) Filed: Nov. 21, 2017

(65) Prior Publication Data
US 2018/0074049 A1 Mar. 15, 2018

Related U.S. Application Data

(63) Continuation of application No. 14/150,207, filed on Jan. 8, 2014, now abandoned.

(60) Provisional application No. 61/749,960, filed on Jan. 8, 2013.

(51) Int. Cl.
*G01N 33/543* (2006.01)
*G01N 33/68* (2006.01)

(52) U.S. Cl.
CPC ... *G01N 33/54326* (2013.01); *G01N 33/6845* (2013.01)

(58) Field of Classification Search
CPC .................... G01N 33/54326; G01N 33/6845
See application file for complete search history.

(56) References Cited

U.S. PATENT DOCUMENTS

| | | | |
|---|---|---|---|
| 7,572,640 B2 | 8/2009 | Goix et al. | |
| 7,838,250 B1 | 11/2010 | Goix et al. | |
| 2002/0164659 A1* | 11/2002 | Rao | C12Q 2563/143 435/7.5 |
| 2007/0166835 A1* | 7/2007 | Bobrow | G01N 35/028 436/174 |
| 2008/0206757 A1* | 8/2008 | Lin | G01N 33/54346 435/6.14 |

OTHER PUBLICATIONS

Griwatz et al. (Journal of immunological methods 183.2 (1995): 251-265) (Year: 1995).*
Loke et al.( Clinical genetics 81.3 (2012): 272-277; accepted manuscript online Dec. 15, 2011) (Year: 2011).*
Kim et al.( Lab Chip, 2005, 5, 657-664). (Year: 2005).*
Wilson et al.( ACS nano 1.5 (2007): 487-493.) (Year: 2007).*
de Jager et al. (Clinical and Diagnostic Laboratory Immunology, Jan. 2003, p. 133-139). (Year: 2003).*
Schmidt et al.(Methods 48.3 (2009): 240-248.) (Year: 2009).*
Quail et al. (Nature methods 5.12 (2008): 1005.) . (Year: 2008).*
Quail 2008 supp (Year: 2008).*
Loke J. et al., entitled "Mutations in MAP3K1 tilt the balance from SOX9/FGF9 to WNT/Beta-cetenin signaling.", Human Molecular Genetics, 2013, 1-11.
PCT Written Opinion of the International Searching Authority dated Nov. 24, 2015 in connection with PCT International Patent Application No. PCT/US15/45856, 9 pages.
Schmidt et al. (methods 48.3 (2009): 240-248.).
Loke et al. (Clincal genetics 81.3 (2012): 272-277: accepted manuscript online Dec. 15, 2011).
Kim et al. (Lab Chip, 2005, 5, 657-664).
Wilson et al. (ACS nano 1.5 (2007): 487-493.).
de Jager et al. (Clin Vaccine immunol Jan. 2003 vol. 10 No. 1 133-139).

* cited by examiner

*Primary Examiner* — Sahana S Kaup
(74) *Attorney, Agent, or Firm* — Scully, Scott, Murphy & Presser, P.C.

(57) ABSTRACT

Methods and compositions are disclosed for rapid functional analysis of gene variants based on analysis of protein-protein and protein-nucleic acid interactions.

19 Claims, 9 Drawing Sheets

A    RHOA FCM IP

B
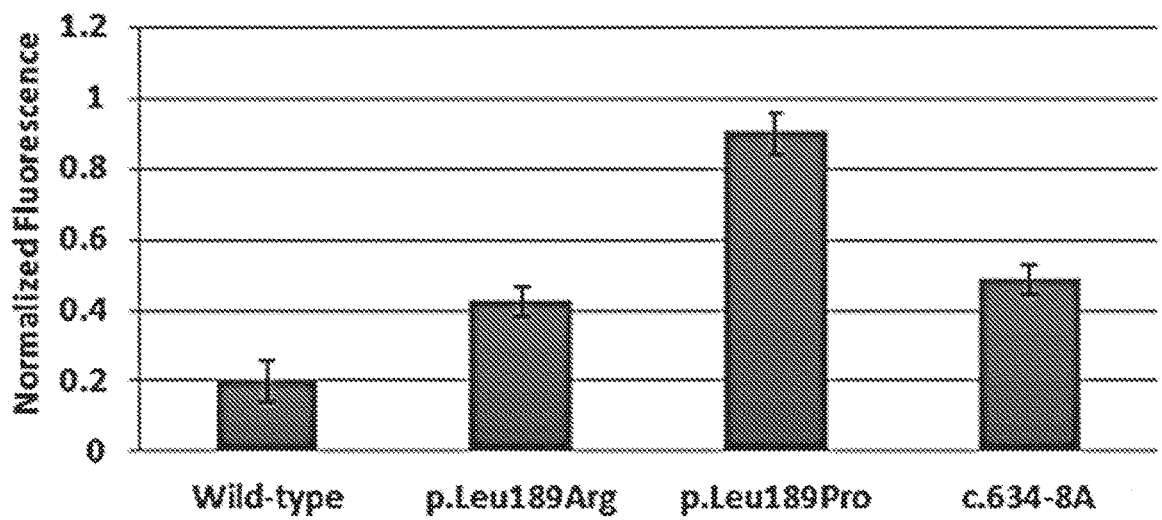
C
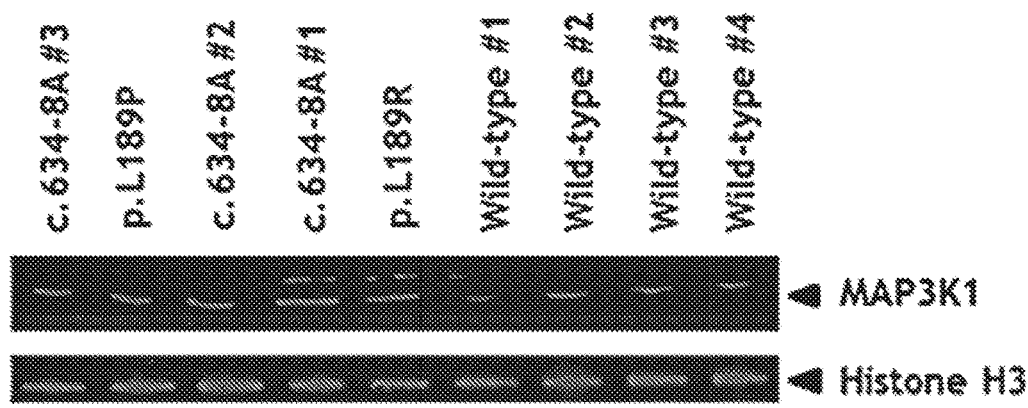
Fig. 5B-C

A.

B.

METHODS AND COMPOSITIONS FOR RAPID FUNCTIONAL ANALYSIS OF GENE VARIANTS

CROSS-REFERENCE TO RELATED APPLICATIONS

This application claims benefit of U.S. Provisional Application No. 61/749,960, filed Jan. 8, 2013, the contents of which are hereby incorporated by reference.

FIELD OF THE INVENTION

The invention relates to methods and compositions for rapid functional analysis of gene variants based on protein-protein and protein-nucleic acid interactions.

BACKGROUND OF THE INVENTION

Throughout this application various publications are referred to in parentheses. Full citations for these references may be found at the end of the specification before the claims. The disclosures of these publications are hereby incorporated by reference in their entireties into the subject application to more fully describe the art to which the subject application pertains.

The availability of accurate, relatively low-cost sequencing methods to analyze the exome or whole genome for novel, rare variants that affect phenotypes has become a game changer in clinical genetics (1). Deciphering the newly identified variants is not a simple task. For any individual genome, up to 3.5 million single nucleotide variants and 600,000 indels may be identified (2). Similarly for any given exome, up to 17,000 variants may be identified (3). To reduce the complexity of analysis, variants are filtered using bioinformatics for rarity by comparison with catalogs, such as dbSNP and 1000 genomes (3-4). Yet, observing a hit in these catalogs does not negate a possible phenotypic effect biologically. Current gold standard computational methods, such as NNSPLICE that predicts splicing alteration (5), and SIFT, SNAP and PolyPhen that predict possible deleterious effects based on conservation of encoded amino acids may also fall short for both sensitivity and specificity (6-8). Linkage, homozygosity mapping and other purely genetic methods may lack statistical power from limited number of affected individuals within a pedigree or community available for study. Furthermore, demonstration of linkage even at a very high LOD score does not preclude the presence of a second variant in linkage disequilibrium that is in fact causal. The observation that 85% of previously identified causal variants for monogenic disorders were identified in exons or at splice-junction boundaries in introns strongly suggests that the vast majority affect the quantity and/or function of the encoded gene RNA and/or protein products (9). In addition, most active proteins are members of multimeric complexes (10). Thus, mutations in a candidate gene may change the quantity of the protein that it encodes, may alter the post-translational modification of that protein or may affect its interaction and localization with its crucial protein binding partners altogether. All three of these alterations can be assessed by immunoassays, which have been a mainstay for quantifying unmodified and modified proteins for over 30 years (11). These methods include both immunohistochemical studies of cells and Western blots of cell homogenates. Dual immunoassays, such as those provided by co-immunoprecipitation (co-IP) followed by Western blots have become important for quantifying protein-protein interactions as functional studies (12).

The present invention addresses the need for rapid functional analysis of gene variants for phenotype effects based on protein-protein and protein-nucleic acid interactions and localization.

SUMMARY OF THE INVENTION

A method is provided for multiplex detecting a first protein-second protein interaction, in a sample, for up to four distinct first proteins, first proteins A, B, C and D respectively, the method comprising:

contacting the sample with a (i) a first agent attached to a surface of a magnetic bead that is not labeled with a first primary optically-active label, and (ii) a second primary agent attached to a surface of a magnetic bead that is labeled with a first primary optically-active label, and (iii) a third primary agent attached to a surface of a non-magnetic bead that is not labeled with a second primary optically-active label, and (iv) a fourth primary agent attached to the surface of a non-magnetic bead that is labeled with a second primary optically-active label, wherein the first, second, third and fourth primary agents are different agents each capable of capturing the distinct first proteins A, B, C and D, respectively;

contacting captured first protein-second protein complex(es) with a plurality of secondary agents each specific for a distinct second protein, and each labeled with a separate secondary optically-active label wherein the secondary optically-active labels are not the same as the primary optically-active labels of the primary agents and are each distinct from the secondary optically-active label of every other of the optically-active labeled secondary agents;

recovering magnetic beads complexes from the sample by applying a magnetic field;

recovering non-magnetic bead complexes from the sample based on a non-magnetic physical property of the non-magnetic beads;

passing the recovered magnetic bead complexes through a flow cytometer or optical plate reader;

passing the recovered non-magnetic bead complexes through a flow cytometer or optical plate reader;

detecting the optical signal(s) of the recovered magnetic bead complexes; and detecting the optical signal(s) of the recovered non-magnetic bead complexes;

wherein the presence on a magnetic bead complex of only a secondary optically-active label indicates the interaction between the first protein A and a second protein corresponding to the secondary optically-active labeled secondary agent, and wherein the presence on a magnetic bead complex of both (i) a first primary optically-active label and (ii) a secondary optically-active label indicates the interaction of the first protein B and a second protein corresponding to the secondary optically-active labeled secondary agent, and wherein the presence on a non-magnetic bead complex of only a secondary optically-active label indicates the interaction of the first protein C and a second protein corresponding to the secondary optically-active secondary labeled agent, and wherein the presence on a non-magnetic bead complex of both (i) a second primary optically-active label and (ii) a secondary optically-active label indicates the interaction of the first protein D and a second protein corresponding to the secondary optically-active labeled secondary agent.

Also provided is a method of multiplex detecting a first protein-second protein interaction, in a sample, for up to at least four distinct first proteins, first proteins A, B, C and D respectively, the method comprising:

contacting the sample with a (i) a first agent attached to a surface of a magnetic bead that is not labeled with a first primary optically-active label, and (ii) a second primary agent attached to a surface of a magnetic bead that is labeled with a first primary optically-active label, and (iii) a third primary agent attached to a surface of a non-magnetic bead that is not labeled with a second primary optically-active label, and (iv) a fourth primary agent attached to the surface of a non-magnetic bead that is labeled with a second primary optically-active label, wherein the first, second, third and fourth primary agents are different agents each capable of capturing the distinct first proteins A, B, C and D, respectively;

contacting captured first protein-second protein complex(es) with a plurality of secondary agents, each of the plurality being specific for a distinct second protein, and each labeled with a separate secondary optically-active label wherein the secondary optically-active labels are not the same as the primary optically-active labels of the primary agents and are each distinct from the secondary optically-active label of every other of the optically-active labeled secondary agents;

recovering magnetic beads complexes from the sample by applying a magnetic field;

recovering non-magnetic bead complexes from the sample based on a non-magnetic physical property of the non-magnetic beads;

passing the recovered magnetic bead complexes through a flow cytometer or optical plate reader;

passing the recovered non-magnetic bead complexes through a flow cytometer or optical plate reader;

detecting the optical signal(s) of the recovered magnetic bead complexes; and detecting the optical signal(s) of the recovered non-magnetic bead complexes;

wherein the presence on a magnetic bead complex of only a secondary optically-active label indicates the interaction between the first protein A and a second protein corresponding to the secondary optically-active labeled secondary agent, and wherein the presence on a magnetic bead complex of both (i) a first primary optically-active label and (ii) a secondary optically-active label indicates the interaction of the first protein B and a second protein corresponding to the secondary optically-active labeled secondary agent, and wherein the presence on a non-magnetic bead complex of only a secondary optically-active label indicates the interaction of the first protein C and a second protein corresponding to the secondary optically-active secondary labeled agent, and wherein the presence on a non-magnetic bead complex of both (i) a second primary optically-active label and (ii) a secondary optically-active label indicates the interaction of the first protein D and a second protein corresponding to the secondary optically-active labeled secondary agent.

Also provided is a method of multiplex detecting a protein-nucleic acid interaction, in a sample, for up to four distinct proteins, proteins A, B, C and D respectively, the method comprising:

contacting the sample with a (i) a first agent attached to a surface of a magnetic bead that is not labeled with a first primary optically-active label, and (ii) a second primary agent attached to a surface of a magnetic bead that is labeled with a first primary optically-active label, and (iii) a third primary agent attached to a surface of a non-magnetic bead that is not labeled with a second primary optically-active label, and (iv) a fourth primary agent attached to the surface of a non-magnetic bead that is labeled with a second primary optically-active label, wherein the first, second, third and fourth primary agents are different agents each capable of capturing the distinct first proteins A, B, C and D, respectively, under conditions which permit capturing to the primary agents a first protein-nucleic acid complex from the sample;

contacting captured first protein-nucleic acid complex(es) with a plurality of secondary agents each specific for a distinct nucleic acid, and each labeled with a separate secondary optically-active label wherein the secondary optically-active labels are not the same as the primary optically-active labels of the primary agents and are each distinct from the secondary optically-active label of every other optically-active labeled secondary agent;

recovering magnetic beads complexes from the sample by applying a magnetic field;

recovering non-magnetic bead complexes from the sample based on a non-magnetic physical property of the non-magnetic beads;

passing the recovered magnetic bead complexes through a flow cytometer or optical plate reader;

passing the recovered non-magnetic bead complexes through a flow cytometer or optical plate reader;

quantifying the optical signal(s) of the recovered magnetic bead complexes; and quantifying the optical signal(s) of the recovered non-magnetic bead complexes;

wherein the presence on a magnetic bead complex of only a secondary optically-active label indicates the interaction between the first protein A and a nucleic acid corresponding to the secondary optically-active labeled secondary agent, and wherein the presence on a magnetic bead complex of both (i) a first primary optically-active label and (ii) a secondary optically-active label indicates the interaction of the first protein B and a nucleic acid corresponding to the secondary optically-active labeled secondary agent, and wherein the presence on a non-magnetic bead complex of only a secondary optically-active label indicates the interaction of the first protein C and a nucleic acid corresponding to the secondary optically-active secondary labeled agent, and wherein the presence on a non-magnetic bead complex of both (i) a second primary optically-active label and (ii) a secondary optically-active label indicates the interaction of the first protein D and a nucleic acid corresponding to the secondary optically-active labeled secondary agent.

The invention provides methods of analyzing a gene variant based on endogeneous or transient protein-protein interaction, the method comprising: attaching a first primary agent to the surface of magnetic beads that are not labeled with an optically active label, such as for example, but not limited to, a fluorescent label, and attaching a second primary agent to the surface of magnetic beads that are labeled with an optically active label; attaching a third primary agent to the surface of non-magnetic beads that are not labeled with an optically active label and attaching a fourth primary agent to the surface of non-magnetic beads that are labeled with an optically active label, wherein the first, second, third and fourth primary agents are different agents and wherein the first, second, third and fourth primary agents are each capable of capturing a distinct protein complex from a cell or tissue lysate; capturing to the primary agents a protein complex from a cell or tissue lysate, where the protein complex comprises a protein of interest that is a product of a gene or a gene variant and where the protein of interest is part of a complex with another protein; probing the protein-protein complex with one or more optically active labeled secondary agents specific for a member of the complex; wherein the same one or more optically active labels can be used to label secondary agents on any of i) the magnetic beads that are not labeled with an optically active label, ii) the magnetic beads that are labeled with an optically active label, iii) the non-magnetic beads that are not labeled with an optically active label, and iv) the non-magnetic beads that are labeled with an optically active label; separating magnetic beads from the lysate based on magnetic properties of the magnetic beads; separating non-magnetic beads from the lysate based on a physical property of the non-magnetic beads; and measuring optical activity of optically active agents, wherein the absence or presence of the optically active label on the magnetic beads is used as an identifier to distinguish optically active protein complexes captured by the first and second primary agents, respectively, and wherein the absence or presence of the optically active label on the non-magnetic beads is used as an identifier to distinguish optically active protein complexes captured by the third and fourth primary agents, respectively.

The invention also provides methods of analyzing a gene variant based on endogenous or transient protein-nucleic acid interaction, the method comprising: attaching a first primary agent to the surface of magnetic beads that are not labeled with an optically active label and attaching a second primary agent to the surface of magnetic beads that are labeled with an optically active label; attaching a third primary agent to the surface of non-magnetic beads that are not labeled with an optically active label and attaching a fourth primary agent to the surface of non-magnetic beads that are labeled with an optically active label, wherein the first, second, third and fourth primary agents are different agents and wherein the first, second, third and fourth primary agents are each capable of capturing a distinct protein-nucleic acid complex from a cell or tissue lysate; capturing to the primary agents a protein-nucleic acid complex from a cell or tissue lysate, where the protein-nucleic acid complex comprises a gene or a gene variant nucleic acid sequence; separating magnetic beads from the lysate based on magnetic properties of the magnetic beads; separating non-magnetic beads from the lysate based on a physical property of the non-magnetic beads; optionally digesting nucleic acids with nucleases prior to digesting proteins on protein-nucleic acid complexes to release nucleic acids; and amplifying the released nucleic acids; wherein the absence or presence of the optically active label on the magnetic beads is used to distinguish optically active protein-nucleic complexes captured by the first and second primary agents, respectively, and wherein the absence or presence of the optically active label on the non-magnetic beads is used to distinguish optically active protein-nucleic acid complexes captured by the third and fourth primary agents, respectively.

The invention effectively incorporate methods for optimal detection and selection of various targets (more than two) with limited starting biomaterial. The invention includes a gating principle that substantially increases sensitivity of the detection of flow cytometry-based immunoassay with no amplification steps of any sort.

The invention provides kits for identification of the protein-protein interactions, protein-nucleic acid interactions, cell-based protein expression, protein modifications, localization and a standard concurrent immunoprecipitation (IP)-Western. The kits allow a simplified flow-based immunoassay that is truly high-throughput and unified sample processing techniques. The kits contain optimized comprehensive chemistries and significant improvement over traditional methods of IP-Western blots.

The kit provides versatility to perform multiple assays, assays such as Digital Cell Western (DCW), rapid assessment of protein-protein interaction and localization by modified flow cytometry-based IP, simplified protein-nucleic acid interactions assessment and captured nucleic acid purification for massive parallel sequencing (MPS), genotyping and polymerase chain reactions (PCR) applications.

DCW, a form of digital Western in this kit that is designed and optimized to probe individual cells for various target protein expressions including post-translational modifications that can be effortlessly detected simultaneously allowing thousands of data points from each fixed cell samples to be aggregated as digital calculation for statistical power.

The invention utilizes a combination of bar-coded bead system, for example but not limited to surface enhanced-Dynabeads and Carboxyl modified beads (CML) to detect multiple variant protein interactions from a single lysate. With the paramagnetic properties of Dynabeads, first separation phase allows clearance of targets bound to the Dynabeads by magnetic separation, remaining supernatant containing CML beads will capture another set of targets that will be separated by centrifugal force. This approach using bar-coded bead systems allows doubling of the number of detected targets with this methodology in various high-throughput formats.

The invention allows assessment of protein-nucleic acid interactions and purification of bound nucleic acids sequences, which is suitable for use in Chromatin Immuno-precipitation (CHIP), RNA IP PCR, genotyping and sequencing (MPS). This is first of its kind kit that allows assessment of variant protein interactions and simultaneous purification of any binding nucleic acid sequences to the variant proteins. Applications such as CHIP, CHIP-sequencing, and RNA IP are transformed into a streamlined assay suitable for large-scaled investigation of various targets in research and diagnostic applications.

Also provided is a method of multiplex detecting a protein-nucleic acid interaction, in a sample, for up to at least four distinct proteins, proteins A, B, C and D respectively, the method comprising:

a) contacting the sample with a (i) a first agent attached to a surface of a magnetic bead that is not labeled with a first primary optically-active label, and (ii) a second primary agent attached to a surface of a magnetic bead that is labeled with a first primary optically-active label, and (iii) a third primary agent attached to a surface of a non-magnetic bead that is not labeled with a second primary optically-active label, and (iv) a fourth primary agent attached to the surface of a non-magnetic bead that is labeled with a second primary optically-active label, wherein the first, second, third and fourth primary agents are different agents each capable of capturing the distinct first proteins A, B, C and D, respectively, under conditions which permit capturing to the primary agents a first protein-nucleic acid complex from the sample;

b) optionally, contacting one or more of the four distinct proteins of the sample with one or more nucleic acids either prior to a) or subsequent to a);

c) recovering magnetic beads complexes from the sample by applying a magnetic field and recovering non-magnetic bead complexes from the sample based on a non-magnetic physical property of the non-magnetic beads;

d) contacting one or more of (i) the magnetic beads complexes not having a first primary optically-active label; (ii) the magnetic beads complexes having a first primary optically-active label; (iii) the non-magnetic beads complexes not having a first primary optically-active label; (iv) the non-magnetic beads complexes having a first primary optically-active label, with optional nuclease then a Proteinase K so as to digest the proteins thereon and release any nucleic acids bound thereto;

e) sequencing nucleic acid(s) released in step d)(i) so as to thereby identify the nucleic acids that have interacted with the first distinct protein; in step d)(ii) so as to thereby identify the nucleic acids that have interacted with the second distinct protein; in step d)(iii) so as to thereby identify the nucleic acids that have interacted with the third distinct protein; and/or in step d)(iv) so as to thereby identify the nucleic acids that have interacted with the fourth distinct protein.

BRIEF DESCRIPTION OF THE DRAWINGS

FIG. 5A-5C. Reverse FVA performed on B-lymphoblastoid cells from wild-type and p.Leu189Arg using the RHOA bait antibody and the Alexa 488-labeled MAP3K1 target antibody. A. The flow cytometry gated results shows increased binding of mutant MAP3K1 to RHOA complexes. B. Results compiled from three independent experiments for each pathogenic mutation, Leu189Arg, p.Leu189Pro and c.634-8A, show increased mutant MAP3K1 binding to RHOA ($p<0.05$). C. Conventional IP Western blots of primary B-lymphoblastoid cells detect an approximate 2.5-fold increase of binding of mutant MAP3K1 to RHOA from all three mutant cell lines compared to wild-type.

DETAILED DESCRIPTION OF THE INVENTION

Figure 1:
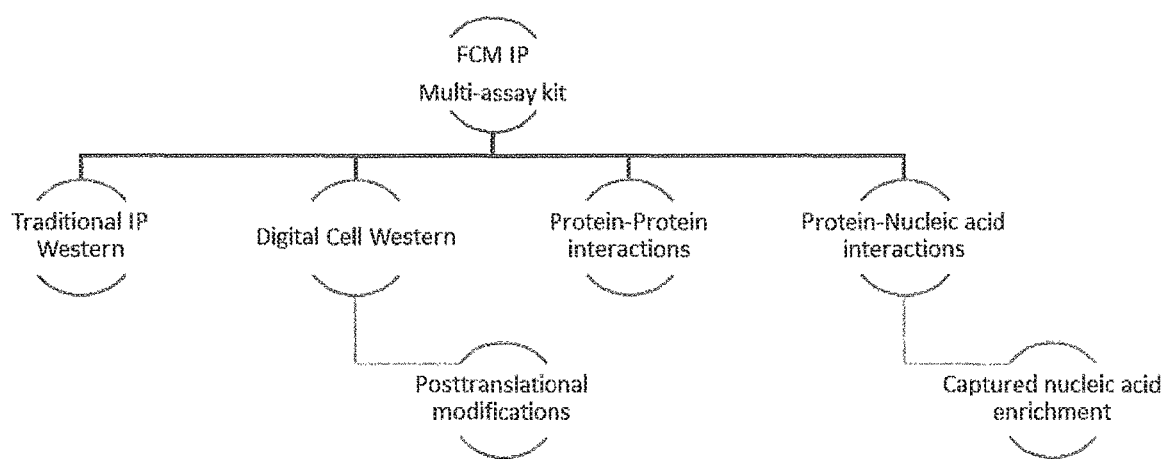
FIG. 1. Application areas of Functional Variant Assay (FVA) kit. The kit provides versatility using flow cytometry to perform multiple assays, such as Digital Cell Western (DCW) concurrent with traditional IP western, rapid assessment of protein-protein interactions of various target using limited biomaterial, protein-nucleic acid interactions assessment, bound nucleic acid purification and enrichment for MPS, genotyping and polymerase chain reactions (PCR) applications. DCW is a form of digital western in this kit that is designed and optimized to probe individual cells for various target protein expressions including post-translational modifications can be effortlessly detected, while simultaneously measuring thousands of data points from each of the fixed cell samples; data points then can be aggregated as digital calculations for statistical power.
Figure 2:
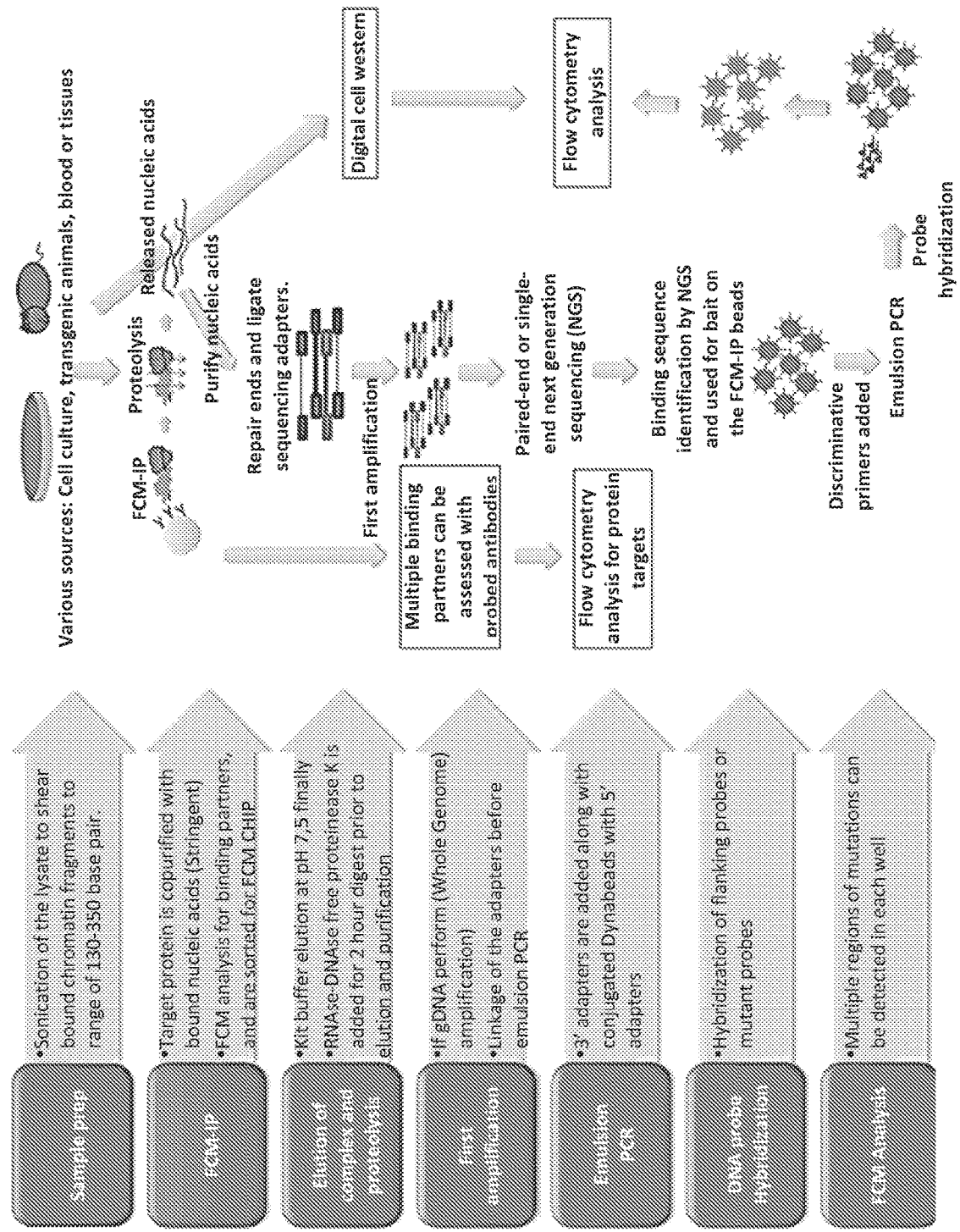
FIG. 2. Examples of application of the invention. The invention allows assessment by modified flow immunoprecipitation of protein-protein interactions, protein-nucleic acid interactions and purification with enrichment of bound/captured nucleic acids sequences suitable for use in PCR, genotyping and sequencing (MPS). The kit allows concurrent assessment of variant protein interactions, digital cell western and simultaneous purification of any binding nucleic acid sequences to the variant proteins for MPS. Applications such as Chromatin Immunoprecipitation (CHIP), CHIP-sequencing, and RNA IP are transformed into a streamlined assay suitable for large-scaled investigation of various targets in research and diagnostic applications.
Figure 3:
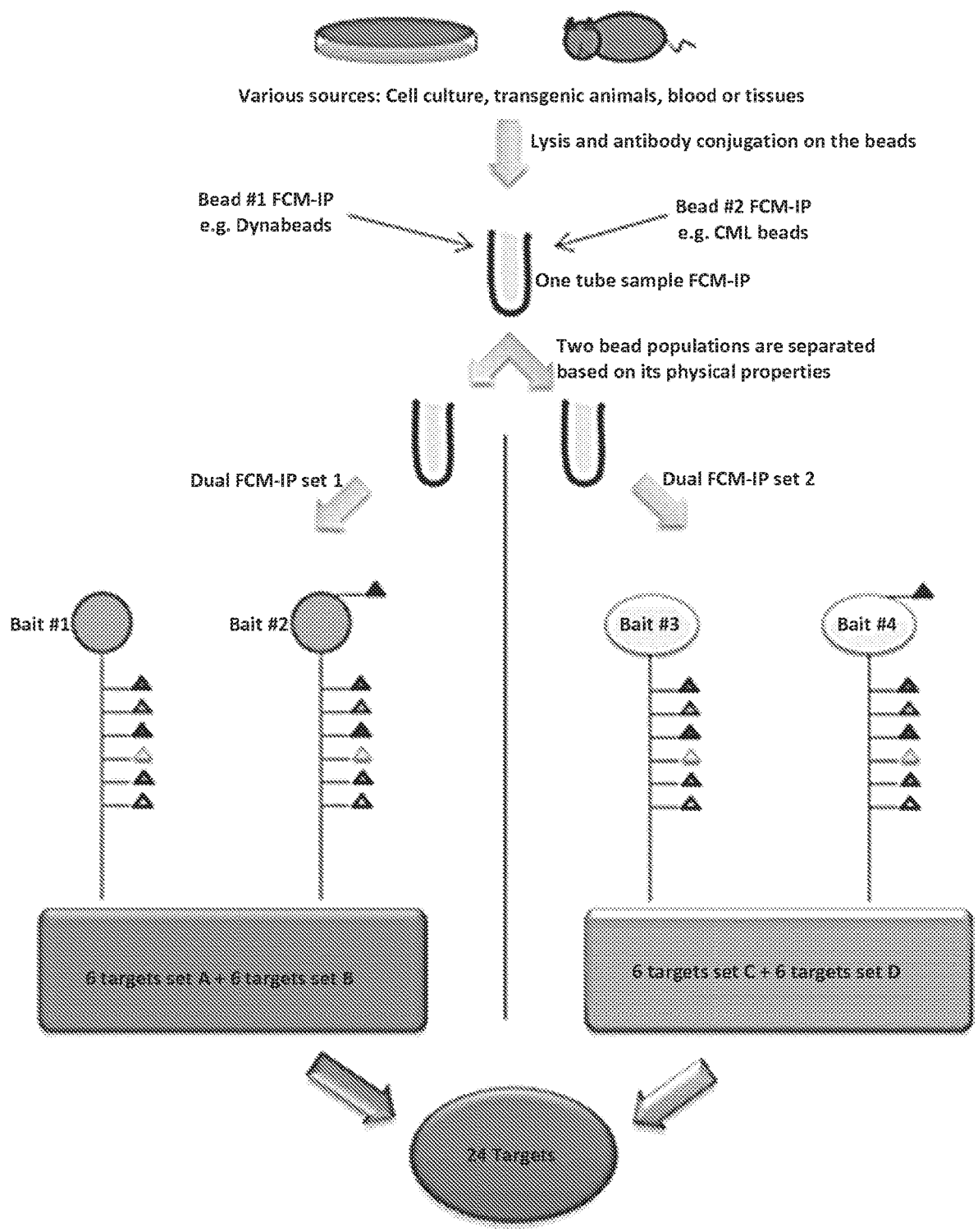
FIG. 3. Example of scheme of the present invention. The invention utilizes a combination of beads, for example but not limited to epoxy Dynabeads and Carboxyl modified beads (CML) to detect multiple variant proteins. With the paramagnetic properties of Dynabeads, a first separation phase allows clearance of targets bound to the Dynabeads by magnetic separation, remaining supernatant containing CML beads will capture another set of targets that will be separated by centrifugal force. This approach using two-bead system will double the number of detected targets using existing methodology optimized for high-throughput analysis. Bar coding complexes to identify different protein-protein complexes or different protein-nucleic acid complexes on beads with different optically active labels ("vertical bar coding"). Another form of bar-coding means to identify different analytes on the magnetic beads and/or non-magnetic beads using optically active labels, for example but not limited to fluorescent labels ("horizontal bar coding"). For example but not limited to, for 7 different fluorescent labels, one label can be used to identify a portion and/or subset of magnetic or non-magnetic beads and the remaining 6 labels can be used to label different protein targets or different protein-nucleic acid complexes attached to the beads. This method is expandable depending on the capabilities and the number of available lasers on the flow cytometer or plate readers.

A method is provided of multiplex detecting a first protein-second protein interaction, in a sample, for up to at least four distinct first proteins, first proteins A, B, C and D respectively, the method comprising:

contacting the sample with a (i) a first agent attached to a surface of a magnetic bead that is not labeled with a first primary optically-active label, and (ii) a second primary agent attached to a surface of a magnetic bead that is labeled with a first primary optically-active label, and (iii) a third primary agent attached to a surface of a non-magnetic bead that is not labeled with a second primary optically-active label, and (iv) a fourth primary agent attached to the surface of a non-magnetic bead that is labeled with a second primary optically-active label, wherein the first, second, third and fourth primary agents are different agents each capable of capturing the distinct first proteins A, B, C and D, respectively;

contacting captured first protein-second protein complex(es) with a plurality of secondary agents each specific for a distinct second protein, and each labeled with a separate secondary optically-active label wherein the secondary optically-active labels are not the same as the primary optically-active labels of the primary agents and are each distinct from the secondary optically-active label of every other of the optically-active labeled secondary agents;

recovering magnetic beads complexes from the sample by applying a magnetic field;

recovering non-magnetic bead complexes from the sample based on a non-magnetic physical property of the non-magnetic beads;

passing the recovered magnetic bead complexes through a flow cytometer or optical plate reader and quantifying the optical signal emitted therefrom;

passing the recovered non-magnetic bead complexes through a flow cytometer or optical plate reader and quantifying the optical signal emitted therefrom;

detecting the optical signal(s) of the recovered magnetic bead complexes; and detecting the optical signal(s) of the recovered non-magnetic bead complexes;

wherein the presence on a magnetic bead complex of only a secondary optically-active label indicates the interaction between the first protein A and a second protein corresponding to the secondary optically-active labeled secondary agent, and wherein the presence on a magnetic bead complex of both (i) a first primary optically-active label and (ii) a secondary optically-active label indicates the interaction of the first protein B and a second protein corresponding to the secondary optically-active labeled secondary agent, and wherein the presence on a non-magnetic bead complex of only a secondary optically-active label indicates the interaction of the first protein C and a second protein corresponding to the secondary optically-active secondary labeled agent, and wherein the presence on a non-magnetic bead complex of both (i) a second primary optically-active label and (ii) a secondary optically-active label indicates the interaction of the first protein D and a second protein corresponding to the secondary optically-active labeled secondary agent.

A method of multiplex detecting a first protein-second protein interaction, in a sample, for up to at least four distinct first proteins, first proteins A, B, C and D respectively, the method comprising:

contacting the sample with a (i) a first agent attached to a surface of a magnetic bead that is not labeled with a first primary optically-active label, and (ii) a second primary agent attached to a surface of a magnetic bead that is labeled with a first primary optically-active label, and (iii) a third primary agent attached to a surface of a non-magnetic bead that is not labeled with a second primary optically-active label, and (iv) a fourth primary agent attached to the surface of a non-magnetic bead that is labeled with a second primary optically-active label, wherein the first, second, third and fourth primary agents are different agents each capable of capturing the distinct first proteins A, B, C and D, respectively;

contacting captured first protein-second protein complex(es) with a plurality of secondary agents, each of the plurality being specific for a distinct second protein, and each labeled with a separate secondary optically-active label wherein the secondary optically-active labels are not the same as the primary optically-active labels of the primary agents and are each distinct from the secondary optically-active label of every other of the optically-active labeled secondary agents;

recovering magnetic beads complexes from the sample by applying a magnetic field;

recovering non-magnetic bead complexes from the sample based on a non-magnetic physical property of the non-magnetic beads;

passing the recovered magnetic bead complexes through a flow cytometer or optical plate reader;

passing the recovered non-magnetic bead complexes through a flow cytometer or optical plate reader;

detecting the optical signal(s) of the recovered magnetic bead complexes; and detecting the optical signal(s) of the recovered non-magnetic bead complexes;

wherein the presence on a magnetic bead complex of only a secondary optically-active label indicates the interaction between the first protein A and a second protein corresponding to the secondary optically-active labeled secondary agent, and wherein the presence on a magnetic bead complex of both (i) a first primary optically-active label and (ii) a secondary optically-active label indicates the interaction of the first protein B and a second protein corresponding to the secondary optically-active labeled secondary agent, and wherein the presence on a non-magnetic bead complex of only a secondary optically-active label indicates the interaction of the first protein C and a second protein corresponding to the secondary optically-active secondary labeled agent, and wherein the presence on a non-magnetic bead complex of both (i) a second primary optically-active label and (ii) a secondary optically-active label indicates the interaction of the first protein D and a second protein corresponding to the secondary optically-active labeled secondary agent.

Such methods may be termed "PrCo-IP." In an embodiment, the plurality of secondary agents is up to twelve secondary agents. In an embodiment, the plurality of secondary agents is up to twenty-four secondary agents. In an embodiment, the plurality of secondary agents is up to thirty-six secondary agents. In an embodiment, the plurality of secondary agents is, not limited to, up to thirty-eight secondary agents. The method may be performed with as many types of secondary agents as are discretely distinguishable.

The method can further comprise multiplex detecting more than four distinct proteins. For detecting n distinct proteins, the magnetic and non-magnetic bead populations must comprise between them a primary agent for each of the n proteins and at least n−2 primary optically-active labels, one for each of n−2 of the proteins. The remaining 2 proteins can be detected by the magnetic and non-magnetic beads which having the primary agent for each of those proteins, but which are unlabeled with the primary optically-active agents.

A method of multiplex detecting protein-nucleic acid interactions in a sample for up to four distinct proteins, proteins A, B, C and D respectively, the method comprising:

a) contacting the sample with a (i) a first agent attached to a surface of a magnetic bead that is not labeled with a first primary optically-active label, and (ii) a second primary agent attached to a surface of a magnetic bead that is labeled with a first primary optically-active label, and (iii) a third primary agent attached to a surface of a non-magnetic bead that is not labeled with a second primary optically-active label, and (iv) a fourth primary agent attached to the surface of a non-magnetic bead that is labeled with a second primary optically-active label, wherein the first, second, third and fourth primary agents are different agents each capable of capturing the distinct proteins A, B, C and D, respectively, under conditions which permit capturing to the primary agents a first protein-nucleic acid complex from the sample;

b) recovering magnetic beads complexes from the sample by applying a magnetic field and recovering non-magnetic bead complexes from the sample based on a non-magnetic physical property of the non-magnetic beads;

c) contacting one or more of (i) the magnetic bead complexes not having a first primary optically-active label; (ii) the magnetic bead complexes having a first primary optically-active label; (iii) the non-magnetic bead complexes not having a first primary optically-active label; (iv) the non-magnetic bead complexes having a first primary optically-active label, with a Proteinase K so as to digest the proteins thereon and release any nucleic acids bound thereto;

d) sequencing nucleic acid(s) released in step c)(i) so as to thereby identify the nucleic acids that have interacted with distinct protein A; in step c)(ii) so as to thereby identify the nucleic acids that have interacted with distinct protein B; in step c)(iii) so as to thereby identify the nucleic acids that have interacted with distinct protein C; and/or in step c)(iv) so as to thereby identify the nucleic acids that have interacted with distinct protein D.

Such a method may be termed "NACo-IP." In an embodiment, the method further comprises contacting one or more of the four distinct proteins of the sample with one or more nucleic acids either prior to a) or subsequent to a). It is apparent that in some circumstances the sample will contain proteins-nucleic acid interactions prior to application of the method in which case such a step is not required. In other cases, where the protein(s) of the sample are free of nucleic interaction prior to application of the method, nucleic acids can be contacted with the proteins to determine if the nucleic acids interact with the proteins. In an embodiment, the plurality of secondary agents is up to twelve secondary agents. In an embodiment, the plurality of secondary agents is up to twenty-four secondary agents. In an embodiment, the plurality of secondary agents is up to thirty-six secondary agents. In an embodiment, the plurality of secondary agents is up to thirty-eight secondary agents. The method may be performed with as many types of secondary agents as are discretely distinguishable.

The method can further comprise multiplex detecting more than four distinct protein-nucleic acid interactions. For detecting n distinct protein-nucleic acid interactions, the magnetic and non-magnetic bead populations must comprise between them a primary agent for each of the n proteins.

In an embodiment, the method further comprises digesting the proteins of the protein-nucleic acids with a Proteinase K. In an embodiment, the method further comprises amplifying the nucleic acids released after Proteinase K digestion. In an embodiment, the method is used to identify genetic heterogeneity among a population of cells. In an embodiment, the sample contacted with the primary agents is subsequently contacted with a nuclease to digest nucleic acids that are not interacting/bound to a protein of the sample. In an embodiment, the method further comprises probing the protein-nucleic acid complex(es) with one or more optically active secondary agents each specific for one of distinct first proteins A, B, C and D, so as to identify bead complexes comprising a bead, a distinct protein and a primary agent, and recovering such bead complexes. In an embodiment, the method further comprises comprising after step c) and before step d) passing the recovered magnetic bead complexes through a flow cytometer or optical plate reader and passing the recovered non-magnetic bead complexes through a flow cytometer or optical plate reader; and detecting the optical signal(s) of the recovered magnetic bead complexes and detecting the optical signal(s) of the recovered non-magnetic bead complexes and, optionally, quantifying the optical signal(s) detected so as to thereby quantify the amount of protein-nucleic acid interaction on the bead.

In an embodiment, the method further comprises amplifying the nucleic acids released after contacting with a Proteinase K, but prior to sequencing.

Also provided is a method of multiplex detecting a protein-nucleic acid interaction, in a sample, for up to four distinct proteins, proteins A, B, C and D respectively, the method comprising:

contacting the sample with a (i) a first agent attached to a surface of a magnetic bead that is not labeled with a first primary optically-active label, and (ii) a second primary agent attached to a surface of a magnetic bead that is labeled with a first primary optically-active label, and (iii) a third primary agent attached to a surface of a non-magnetic bead that is not labeled with a second primary optically-active label, and (iv) a fourth primary agent attached to the surface of a non-magnetic bead that is labeled with a second primary optically-active label, wherein the first, second, third and fourth primary agents are different agents each capable of capturing the distinct first proteins A, B, C and D, respectively, under conditions which permit capturing to the primary agents a first protein-nucleic acid complex from the sample;

contacting captured first protein-nucleic acid complex(es) with a plurality of secondary agents each specific for a distinct nucleic acid, and each labeled with a separate secondary optically-active label wherein the secondary optically-active labels are not the same as the primary optically-active labels of the primary agents and are each distinct from the secondary optically-active label of every other optically-active labeled secondary agent;

recovering magnetic beads complexes from the sample by applying a magnetic field;

recovering non-magnetic bead complexes from the sample based on a non-magnetic physical property of the non-magnetic beads;

passing the recovered magnetic bead complexes through a flow cytometer or optical plate reader and quantifying the optical signal emitted therefrom;

passing the recovered non-magnetic bead complexes through a flow cytometer or optical plate reader and quantifying the optical signal emitted therefrom;

quantifying the optical signal(s) of the recovered magnetic bead complexes; and quantifying the optical signal(s) of the recovered non-magnetic bead complexes;

wherein the presence on a magnetic bead complex of only a secondary optically-active label indicates the interaction between the first protein A and a nucleic acid corresponding to the secondary optically-active labeled secondary agent, and wherein the presence on a magnetic bead complex of both (i) a first primary optically-active label and (ii) a secondary optically-active label indicates the interaction of the first protein B and a nucleic acid corresponding to the secondary optically-active labeled secondary agent, and wherein the presence on a non-magnetic bead complex of only a secondary optically-active label indicates the interaction of the first protein C and a nucleic acid corresponding to the secondary optically-active secondary labeled agent, and wherein the presence on a non-magnetic bead complex of both (i) a second primary optically-active label and (ii) a secondary optically-active label indicates the interaction of the first protein D and a nucleic acid corresponding to the secondary optically-active labeled secondary agent.

In an embodiment of the methods, the presence on a bead complex of a first primary optically-active label and/or a secondary optically-active label is determined by quantifying the optical signal thereof.

In an embodiment of the methods, the optical signal is collected with one or more photomultipliers. In an embodiment of the methods the recovered bead complexes are passed through a flow cytometer. In an embodiment of the methods the recovered bead complexes are passed through an optical plate reader.

In an embodiment of the methods, the methods further comprise quantifying the optical signal(s) detected and comparing the quantified amount against a control amount or control curve so as to thereby quantify the amount of first protein-second protein interaction on the bead or the amount of protein-nucleic acid interaction on the bead, as relevant. Such a method may be termed "digital cell Western" or "DCW."

In an embodiment of the methods, each primary agent comprises an antibody or comprises an antigen-binding fragment of an antibody.

In an embodiment of the methods, each secondary agent comprises an antibody or comprises an antigen-binding fragment of an antibody. In an embodiment of the methods, the antibodies are monoclonal antibodies. In an embodiment of the methods, the antibody fragments are F(ab')2 fragments, Fab' fragments or ScFvs.

In an embodiment of the methods, the primary agents comprises an antibody or comprise an antigen-binding fragment of an antibody, and wherein the secondary agents are oligonucleotides that hybridize with a specific sequence of a nucleic acid.

In an embodiment of the methods, the sample is a cell or tissue lysate, or any biological lysates. In an embodiment of the methods, the sample is a cell, and the cell is fixed and permeabilized so as to permit primary and second agent entry into the cell prior to performing the method.

In an embodiment of the methods, the first protein-second protein complex comprises a protein of that is a product of a gene variant.

In an embodiment of the methods, the first proteins A, B, C and D are distinct variant forms of a single protein.

In an embodiment of the methods, the sample contains at least one first distinct protein-second distinct protein interaction.

In an embodiment of the methods, a bead complex comprises the bead having a primary agent attached thereto, wherein the primary agent is attached to a distinct first protein and the distinct first protein is interacting (for example, bound to) a distinct second protein which has bound a labeled secondary agent. In an embodiment of the methods, a first protein-second protein complex is an association of the first protein and second protein (for example, by way of binding to each other).

In an embodiment, the interaction is an intermolecular interaction, occurring by intermolecular forces, such as ionic bonds, hydrogen bonds or van der Waals forces.

A "distinct" protein is one that has a sequence which is non-identical to every other recited "distinct" protein. The distinct proteins referred to herein are distinct in that they have different amino acid sequences. The distinct proteins can be variants, or can be completely different proteins. "Proteins A, B, C and D," or grammatical variations thereof, as referred to herein are not actual protein names, but merely identifiers to distinguish up to four different proteins.

In an embodiment the term "variant," for example, of a gene or a protein, means one having 97%, 98% or 99% or greater (but not 100%) sequence identify with the gene or protein, respectively, that the recited gene or protein is a variant of. In an embodiment the term "variant," for example, of a gene or a protein, means one having 99% or greater (but not 100%) sequence identify with the gene or protein, respectively, that the recited gene or protein is a variant of.

In an embodiment of the methods, forward scatter (FSC) and/or side scatter (SSC) are adjusted with a control uncomplexed bead population prior to initiating the method so as to permit complexed beads to be detected.

In an embodiment of the methods, the ratio of primary agent to primary optically-active labels on primary agents so-labeled is 1:1. In an embodiment of the methods, the ratio of secondary agent to secondary optically-active labels on secondary agents so-labeled is 1:1.

In an embodiment of the methods, the magnetic beads are surface enhanced (e.g. epoxy-coated) magnetic beads. In an embodiment of the methods, the non-magnetic beads are carboxyl modified beads.

In an embodiment of the methods, the agents are attached to the beads by covalent binding.

In an embodiment of the methods, optically-active labels are chosen from the group of fluorophores and nanocrystals.

In an embodiment of the methods, the sample is a lysate and magnetic beads are separated from the lysate using a magnetic field.

In an embodiment of the methods, the optical signal is quantified by first exposing the complexed beads to one or more excitation light sources, such as, in a non-limiting embodiment, a laser. In an embodiment of the methods, the optical signal is quantified by first exposing the complexed beads to one or more lasers.

In an embodiment of the methods, the sample is contacted with the first agent(s) and second agent(s) under conditions which permit capturing to the primary agents a first protein-second protein complex from the sample.

In an embodiment of the methods, the sample is a lysate and the non-magnetic beads are separated from the lysate by centrifugation.

In an embodiment of the methods, the cell or tissue lysate is from primary isolated cells, lymphoblasts, fibroblasts, cancer cells, a cell line, transfected cells, tissue or blood.

In an embodiment of the methods, quantitatively measured optical activity of labeled agents bound to the complex is converted into a relative or an absolute quantitation number of co-binding molecules in each complex.

In an embodiment of the methods, forward scatter amplitude gain and side scatter voltage on a flow cytometer are set to register populations of bead events to on scale, followed by applying an inclusion gate where selected linear populations of beads form collective clusters containing interrogation targets can be analyzed in their entirety by flow cytometry.

Also provided is a kit for detecting changes in protein expression in cells and for analysis of gene variants, the kit comprising:
magnetic beads for immunoprecipitation,
non-magnetic beads for immunoprecipitation,
a lysis formulation,
one or more Proteinase K inhibitors,
one or more phosphatase inhibitors,
a coupling buffer,
nucleic acids recovery elution buffer,
one or more functional variant assay (FVA) buffers,
a Western loading buffer,
one or more optically active labels, and
instructions for use of the kit.

In an embodiment, the kit further comprises one or more of:
a nucleic acid recovery buffer,
a proteinase inhibitor,
a fix-permeabilization buffer, and
one or more primary agents for capturing protein-protein complexes or protein-nucleic acid complexes.

In an embodiment, the optically active labels are nanoparticles and/or fluorescent dyes.

In an embodiment, primary agents are attached to the beads. In an embodiment, a portion and/or subset of the beads are labeled with an optically active agent.

Also provided is a method of detecting and analyzing a gene variant based on a protein-protein interaction, the method comprising:
attaching a first primary agent to the surface of magnetic beads that are not labeled with an optically active label and attaching a second primary agent to the surface of magnetic beads that are labeled with an optically active label;
attaching a third primary agent to the surface of non-magnetic beads that are not labeled with an optically active label and attaching a fourth primary agent to the surface of non-magnetic beads that are labeled with an optically active label, wherein the first, second, third and fourth primary agents are different agents and wherein the first, second, third and fourth primary agents are each capable of capturing a distinct protein complex from a cell or tissue lysate;
capturing to the primary agents a protein complex from a cell or tissue lysate, where the protein complex comprises a protein of interest that is a product of a gene or a gene variant and where the protein of interest forms part of a complex with another protein;
probing the protein-protein complex with one or more optically active secondary agents specific for a member of the complex; wherein the same one or more optically active labels can be used to label secondary agents on any of i) the magnetic beads that are not labeled with an optically active label, ii) the magnetic beads that are labeled with an optically active label, iii) the non-magnetic beads that are not labeled with an optically active label, and iv) the non-magnetic beads that are labeled with an optically active label;
separating protein-magnetic bead complexes from the lysate based on magnetic properties of the magnetic beads;
separating protein-non-magnetic bead complexes from the lysate based on a physical property of the non-magnetic beads; and
measuring optical activity of optically active-labeled agents on the protein-bead complexes,
wherein the absence or presence of the optically active label on the magnetic beads is used to distinguish optically active protein complexes captured by the first and second primary agents, respectively, and
wherein the absence or presence of the optically active label on the non-magnetic beads is used to distinguish optically active protein complexes captured by the third and fourth primary agents, respectively.

Also provided is a method of detecting and/or analyzing a gene variant based on a protein-nucleic acid interaction, the method comprising:
attaching a first primary agent to the surface of magnetic beads that are not labeled with an optically active label and attaching a second primary agent to the surface of magnetic beads that are labeled with an optically active label;
attaching a third primary agent to the surface of non-magnetic beads that are not labeled with an optically active label and attaching a fourth primary agent to the surface of non-magnetic beads that are labeled with an optically active label, wherein the first, second, third and fourth primary agents are different agents and wherein the first, second, third and fourth primary agents are each capable of capturing a distinct protein-nucleic acid complex from a cell or tissue lysate;
capturing to the primary agents a protein-nucleic acid complex from a cell or tissue lysate, where the protein-nucleic acid complex comprises a gene or a gene variant nucleic acid sequence;
separating protein-nucleic acid-magnetic bead complexes from the lysate based on magnetic properties of the magnetic beads;
separating protein-nucleic acid-non-magnetic beads complexes from the lysate based on a physical property of the non-magnetic beads;
digesting proteins on the protein-nucleic acid bead complexes to release nucleic acids; and
amplifying the released nucleic acids;
wherein the absence or presence of the optically active label on the magnetic beads is used to distinguish optically active protein-nucleic complexes captured by the first and second primary agents, respectively, and
wherein the absence or presence of the optically active label on the non-magnetic beads is used to distinguish optically active protein-nucleic acid complexes captured by the third and fourth primary agents, respectively.

The invention provides a method of detecting and/or analyzing a gene variant based on changes of protein-protein interactions, the method comprising:
attaching a first primary agent to the surface of magnetic beads that are not labeled with an optically active label and attaching a second primary agent to the surface of magnetic beads that are labeled with an optically active label;
attaching a third primary agent to the surface of non-magnetic beads that are not labeled with an optically active label and attaching a fourth primary agent to the surface of non-magnetic beads that are labeled with an optically active label, wherein the first, second, third and fourth primary agents are different agents and wherein the first, second, third and fourth primary agents are each capable of capturing a distinct protein complex from a cell or tissue lysate;
capturing to the primary agents a protein complex from a cell or tissue lysate, where the protein complex comprises one or more proteins of interest, where the protein of interest is a product of a gene or a gene variant and where the protein of interest forms a complex with another protein;

probing the protein-protein complex with one or more optically active labeled secondary agents specific for a member of the complex; wherein the same one or more optically active labels can be used to label secondary agents on any of i) the magnetic beads that are not labeled with an optically active label, ii) the magnetic beads that are labeled with an optically active label, iii) the non-magnetic beads that are not labeled with an optically active label, and iv) the non-magnetic beads that are labeled with an optically active label;

separating protein-magnetic bead complexes from the lysate based on magnetic properties of the magnetic beads;

separating protein-non-magnetic bead complexes from the lysate based on a physical property of the non-magnetic beads; and measuring optical activity of optically active-labeled agents probed on the protein-bead complexes, wherein the absence or presence of the optically active label on the magnetic beads is used to distinguish optically active protein complexes captured by the first and second primary agents, respectively, and wherein the absence or presence of the optically active label on the non-magnetic beads is used to distinguish optically active protein complexes captured by the third and fourth primary agents, respectively.

The invention also provides a method of detecting and/or analyzing a gene variant based on changes of protein-nucleic acid interactions, the method comprising:

attaching a first primary agent to the surface of magnetic beads that are not labeled with an optically active label and attaching a second primary agent to the surface of magnetic beads that are labeled with an optically active label;

attaching a third primary agent to the surface of non-magnetic beads that are not labeled with an optically active label and attaching a fourth primary agent to the surface of non-magnetic beads that are labeled with an optically active label, wherein the first, second, third and fourth primary agents are different agents and wherein the first, second, third and fourth primary agents are each capable of capturing a distinct protein-nucleic acid complex from a cell or tissue lysate;

capturing to the primary agents a protein-nucleic acid complex from a cell or tissue lysate, where the protein-nucleic acid complex comprises a gene or a gene variant nucleic acid sequence;

separating protein-nucleic acid-magnetic bead complexes from the lysate based on magnetic properties of the magnetic beads;

separating protein-nucleic acid-non-magnetic bead complexes from the lysate based on a physical property of the non-magnetic beads;

digesting proteins on the protein-nucleic acid complexes to release nucleic acids; and amplifying the released nucleic acids;

wherein the absence or presence of the optically active label on the magnetic beads is used to distinguish optically active protein-nucleic complexes captured by the first and second primary agents, respectively, and wherein the absence or presence of the optically active label on the non-magnetic beads is used to distinguish optically active protein-nucleic acid complexes captured by the third and fourth primary agents, respectively.

In any of the methods disclosed herein, a washing step can be performed between contacting and recovering steps in order to remove unwanted or unbound materials.

In any of the methods or kits disclosed herein, the magnetic beads can be, for example but not limited to, epoxy-coated magnetic beads. In any of the kits or methods disclosed herein, the non-magnetic beads can be, for example but not limited to, carboxyl modified beads. Examples of beads that can be used the methods and kits disclosed herein include, but are not limited to, Dynabeads® M-270, Dynabeads® M-450, Carboxyl Modified Latex Beads and Dynabeads ClinExVivo Epoxy from Invitrogen Corporation, Carlsbad Calif.

Additional agents can be attached the surface of the beads, and protein-protein and protein-nucleic acid complexes, to increase the complexity of the functional assay.

In any of the methods or kits disclosed herein, the agents can be one or more of antibodies, monoclonal antibodies, polyclonal antibodies, antibody fragments, F(ab')$_2$ fragments, Fab' fragments, peptides, nucleotides, peptide nucleic acids, and small biological and/or chemical compounds. The small compound can have a molecular weight of, for example but not limited to, 2,000 daltons or less, e.g., 1,000-2,000 daltons.

In any of the methods or kits disclosed herein, agents can be attached to the beads, for example but not limited to by chemical binding, such as, e.g., covalent binding.

In any of the methods or kits disclosed herein, beads can be labeled with an optically active label by, for example, using an optically active primary agent. Alternatively, or in addition, beads can be labeled with an optically active label by using an optically active agent that is different than the primary agent used to capture protein complexes or protein-nucleic acid complexes.

In any of the methods or kits disclosed herein, the optically active label can be, for example but not limited to, a fluorescent label and/or a nanocrystal (e.g., QDot®).

An optically active label having the same unique wavelength (for example, color green) can be used to label secondary agents on any of i) the magnetic beads that are not labeled with an optically active label, ii) the magnetic beads that are labeled with an optically active label, iii) the non-magnetic beads that are not labeled with an optically active label, and iv) the non-magnetic beads that are labeled with an optically active label. This allows for multiplexing of labels to identify distinct protein-protein and/or protein-nucleic acid complexes.

In any of the methods disclosed herein, the magnetic beads can be separated from the lysate using a magnetic field. In methods disclosed herein, the non-magnetic beads can be separated from the lysate their physical properties, for example but not limited to centrifugation. Alternatively, after the magnetic beads are removed from the lysate, non-magnetic beads can be separated from the lysate by binding (covalent or non-covalent) the non-magnetic beads to secondary magnetic beads and separating the bound non-magnetic/magnetic bead complex using a magnetic field.

In methods disclosed herein, quantitatively measured optical activity of optically active agents bound to the complex can be converted into an absolute or estimated relative number of co-binding molecules in the complex. Optically active beads can be counted by optical readers, for example but not limited to a flow cytometer and/or plate reader.

In methods disclosed herein, the methods can comprise techniques of selecting subpopulation of beads with analyte complex by means of sorting for particular targets of interest based on optical properties for further analysis and/or downstream applications, for example but not limited to purification of the captured analytes.

In methods disclosed herein, forward scatter amplitude gain and side scatter voltage on a flow cytometer can be set to register populations of bead events to on scale, followed by applying an inclusion gate where linear selected populations of beads are analyzed so that complex populations of the collective clusters containing interrogation targets can be analyzed in their entirety by flow cytometry.

In methods disclosed herein, captured/purified nucleic acids can be amplified using any conventional method, e.g., sequencing, polymerase chain reaction, multiplex ligation assay, etc.

In methods disclosed herein, the cell or tissue lysate can be from, e.g., primary isolated cells, such as, lymphoblasts, fibroblasts, normal or diseased tissues, cancer cells or any cell lines not limited to transfected cells and from tissues or blood.

With any of the methods or kits disclosed herein, a wild-type gene can be compared with a gene variant with or without transgene overexpression (exogenous).

The invention provides a kit for detecting changes in protein expression in cells and for analysis of gene variants, the kit comprising:
  magnetic beads for immunoprecipitation,
  non-magnetic beads for immunoprecipitation,
  a lysis formulation,
  one or more Proteinase K inhibitors,
  one or more phosphatase inhibitors,
  a coupling buffer,
  nucleic acids recovery elution buffer,
  one or more (e.g., a set of) functional variant assay (FVA) buffers,
  a Western loading buffer,
  one or more optically active labels, and
  instructions for use of the kit.
The optically active labels can be, for example but not limited to, nanoparticles and/or fluorescent dyes.

The kit can also include, for example, one or more of a nucleic acid recovery buffer (CHIP digest buffer), a protease inhibitor, a fix-permealization buffer, and one or more primary agents for capturing protein-protein complexes or protein-nucleic acid complexes.

The kit can include one or more primary agents for capturing protein-protein complexes or protein-nucleic acid complexes. The primary agents can be attached to the beads. A portion and/or subset f the beads can be labeled with an optically active agent. The kit can include, for example, one or more optically active agents for binding to a protein-protein complex or to a protein-nucleic acid complex.

The kit and methods disclosed herein allow techniques of selecting subpopulation of beads with analyte complex by means of sorting for particular targets of interest for further analysis and/or downstream applications, for example but not limited to purification of the captured analytes.

Examples of phosphatase inhibitors than can be used include, but are not limited to, 10× sodium orthovanadate stock and 10× sodium fluoride stock. Examples of Proteinase K inhibitors than can be used include, but are not limited to, 10× Super Proteinase K inhibitor cocktail. For example, dissolve Proteinase K inhibitor cocktail (Sigma, cat. no. P 2714) in 900 µL distilled $H_2O$. It also contains other inhibitors, for example but not limited to AEBSF (4-(2-aminoethyl) benzenesulfonyl fluoride, Sigma, cat. no. A8456), bestatin, aprotinin, Ethylenediaminetetraacetic acid (EDTA), E-64, and leupeptin. Examples of detergents that can be used include, but are not limited to, nonionic detergent: e.g. Triton X-100, NP-40, and digitonin.

The instructions for use of the kit can include any of the instructions set forth within the present application.

The invention provides kits for the following:
1. Identification of the protein-protein interactions;
    1.1. The kit includes a bar-coded bead system, for example but not limited to epoxy-modified Dynabeads and CML beads, buffers, and recommended optically active agents, for example but not limited to fluorescent dyes (one vial for each conjugate dyes for attaching to an agent, for example but not limited to target antibodies). A complement of buffer system for all steps from fixation, permeabilization and staining of cells, lysis of cells or tissues, protein, FVA washes and flow analysis.
2. Protein-nucleic acid interactions;
    2.1. Gentle elution buffer for active protein-nucleic acid complex purification, and sample recovery after FVA analysis by sorting. The kit includes a protein digestion chemistry in the form of, for example but not limited to, DNase and RNAse-free proteinase K, Upon performing FVA or Flow sorting, population of beads can be precipitated by applying magnetic field, and by physical separation of the second population of beads with another complex. No wash needed. A kit digestion buffer mix is added to the barcoded bead systems for 2 hour or overnight digest to the beads. DNA elution and purification at neutral pH to enrich captured nucleic acids for applications of MPS followed after CHIP, allelic discrimination assays, quantitative PCR expression analysis, RNA IP, RNA CHIP and CHIPs PCR assays.
3. Cell-based protein expression;
    3.1. A digital cell western system (DCW) to fix and permeabilize cells for staining of internal cellular expression of analytes is designed in the kit. This replaces the need to perform separate Western blot prior to IP, or standard westerns.
4. Protein modifications;
    4.1. With the available of antibodies for modified proteins (phosphorylation, acetylation, prenylation, ubiquitination), and other antibodies or agents that can detect modifications of analyte, the kit is design to incorporate these agents as part of the unified assay read out.
5. Concurrent immunoprecipitation (IP)-Western;
    5.1. The recovered beads after FVA analysis can be treated with the kit Western elution buffer containing Sodium dodecyl sulfate (SDS) and dye designed for downstream traditional Western blot. This reduces technical variations when comparing experimental readout data from the same sample.
6. Generation of reference controls using the FVA kit conjugated antibodies;
    6.1. The conjugation buffer is adapted to perform conjugation of the freshly made optically active, for example but not limited to fluorescently labeled, antibodies to the beads rapidly. These are the antibodies that will be used to detect the FVA analytes. This increases consistency as the same host, and recognition epitope as in the detection antibodies are used.

The invention provides methods that include:
1. Methods to identify the protein-protein interactions;
    1.1. Bait antibody is conjugated on to the surface of the epoxy modified beads, a set of optically active multi-analyte antibodies can be used to detect the bound proteins using methods of FVA. This allows identification of proximal binding targets within one complex. FVA allows quantitative measurement of up to various targets simultaneously. With the use of FVA, selection of particular variant interactions can be selected by gating inclusion/exclusion sorter, and be eluted for further assays and other analysis that is otherwise not possible by conventional means. The kit includes steps to use these same analyte agents, such as for example antibodies, to generate optical standards that can be used to accurately establish the threshold of detection based on its optical standard intensities.

2. Methods to identify protein-nucleic acid interactions;
   2.1. A simplified workflow that includes nucleic acid enrichment after FVA by elution of protein-nucleic acid complex, digest, release of nucleic acids and enrichment methods, for example but not limited to ligation of adaptamers to the fragments of captured nucleic acids to perform digital emulsion or standard PCR steps to assess the bound regions to the target sequences and their variants using optical scanners, for example sequencer, flow cytometer or plate reader. The target sequence and its variant forms (single nucleotide polymorphisms, insertions and deletions, and structural rearrangements) can be measured by using optically active probes annealed to the amplified targets on the beads. In addition, the kit allows novel methods to identify binding sites of the RNA with the interacting proteins in its native form, adapted to a high throughput and high content analysis format.

3. Cell-based protein expression (DCW);
   3.1. Prior to lysing of the cells for FVA, a quick assessment of the expression levels of the analyte can be performed by sampling using DCW to fix, permealize, and immunostain the cells. Multiple protein targets can be measured simultaneously. Each detention data point is considered to be one cell western, and aggregate of cells generates a digital value of the cumulative data points, as digital cell western.

4. Protein modifications;
   4.1. DCW methodology is optimized to incorporate available analyte antibodies to detect protein modifications, where the antibodies for specific post translational modification can be conjugated with the optically active agent.

5. Concurrent immunoprecipitate (IP)-Western;
   5.1. Beads that are retained after FVA analysis can be placed into denaturing western loading buffer in the kit to perform standard IP-western blot.

6. Generation of reference controls using the optically active conjugated antibodies;
   6.1. In traditional protocols, prior to performing flow cytometry analysis, a set of commercial bead-based reference dyes is used to create fluorescence standards; drawbacks are commonly acknowledged that the host epitope of antibodies for the analyte is greatly different from the references. The FVA reference control methodology resolve this issue by using the same conjugated antibodies as calibration controls by conjugating them on to the bead systems.

The interaction of the protein of interest ("bait") or variant protein with its associated targets, and multiple gene variant complexes can be examined simultaneously. This has the effect of looking not only at a major effect of a variant in the bait gene(s), but also at the epistatic interactions of a variant in second gene(s) with the bait products of other genes in the complex.

By altering the gating and an inclusion principle of counting a population of subsets of beads previously missed, the present invention greatly improves sensitivity by at least 10-fold. By improving the sensitivity, the amount of starting material can be reduced significantly and by using a bar-coded bead system, the binding time can be reduced dramatically from 24 hours (overnight) to 5 hours for multigene functional assay.

By gating and sorting for analytes of interests, the present invention allows for selection and enrichment of target proteins or nucleic acids that would simply not be possible using current technologies.

The kit provides all the steps and chemical reagents necessary to perform a DCW assay, with addition of one initial startup step, i.e., permeabilize the cells prior to the FVA standard protocol.

As used herein, one form of "bar coding" means to identify different protein-protein complexes or different protein-nucleic acid complexes on beads with different optically active labels ("vertical bar coding"). Another form of bar-coding means to identify different analytes on the magnetic beads and/or non-magnetic beads using optically active labels ("horizontal bar coding"). For example, but not limited to, for 7 different fluorescent labels, one label can be used to identify a portion and/or subset of magnetic or non-magnetic beads and the remaining 6 labels can be used to label different protein-protein complexes or different protein-nucleic acid complexes attached to the beads.

Examples of apparatus that can be used with the disclosed methods include, but are not limited to, a 7-color flow laser machine or a 13-color flow laser.

The methods disclosed herein allow unprecedented speed to study effects of mutations and offers high sensitivity to detect mutant protein activities, such as changes in protein-protein interactions, modifications and mutant protein co-localization into the nucleus. Traditionally, a transgene is needed for each interrogated mutant, whereas the present method uses cells isolated from actual subject bearing the mutation, hence there is no need to create any transgene prior to the FVA assay. In an embodiment of the methods, no transgene is inserted into the cells of the sample. Additionally, conventional methods struggle to detect endogenous protein accurately, but the increased sensitivity of the present methods allow accurate detection of the mutant protein and of its activities. This changes the paradigm of having to genetically engineer mutant cells to study its biology, to simply using the isolated subject cells for various assays described. In an embodiment of the methods, no the cells of the sample have not been previously genetically engineered. The methods herein allow effective cost reduction for large-scaled studies of mutation.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

Example A—Methods

Introduction

The dynamic range of Co-IP Western blots can be improved by flow cytometry, a direct counting function (13). Using this method, immunoprecipitating antibodies, known as 'bait', are coupled covalently to polystyrene beads whose low autofluorescence is suitable for flow cytometry detection. Once coupled, the antibodies on beads will immunoprecipitate a specific protein complex in cell lysates. These complexes can then be probed with a panel of fluorescently tagged secondary antibodies to quantify the binding of the interacting partners by quantitatively count the bound beads on a flow cytometer at high speed. Here, this method has been applied to probe a clinical case study using wild-type B lymphoblastoid cell lines or those derived from patients with MAP3K1 mutations who have 46,XY gonadal dysgenesis (14).

The present studies show altered binding of interacting proteins that could influence downstream signaling in testis or ovarian-determining pathways. Because B cell lines express a large repertoire of protein complexes and can be derived from patients with presumed genetic disorders in a non-invasive manner, they represent a readily available resource for screening variants of uncertain phenotypic significance.

Materials and Methods

Cell Culture and Reagents.

Three MAP3K1 mutation-bearing Epstein-Barr virus B-lymphoblastoid cells lines (c.634-8A, p.Leu189Arg, and p.Leu189Pro) from individuals with 46,XY complete gonadal dysgenesis and a wild-type cell line were derived, as described previously (14). These cell lines were grown in RPMI medium (Invitrogen A2780), supplemented with 15% (v/v) FBS Defined Grade, 50 units/ml penicillin, and 50 g/ml streptomycin at 37° C. with 5% $CO_2$. The antibodies included MAP3K1 rabbit polyclonal antibody (Lifetech #51-340), RHOA rabbit polyclonal antibody (Abcam #ab66124), MAP3K4 mouse monoclonal (Abcam #55669), IRDye 800CW Goat anti-Mouse (Licor #926-32210), and IRDye 680LT Goat anti-Rabbit IgG (Licor #926-68021). Western blotting analysis was performed as described previously (14).

FVA on Cultured Lymphoblastoid Cells.

FVA was performed with the following modifications optimized for lymphoblastoid cell lysates. The bait antibody was conjugated onto epoxy modified beads at concentrations of 30 µg of antibody per mg of 5 micron epoxy beads, conjugation is achieved using the coupling buffers in the kit. The Proteinase K and phosphatase inhibitors at 2 or 4× concentration were added to the cell lysates during lysis. Antibody conjugated epoxy beads were added to the lysates to incubate for 5 hours or overnight at 4° C. Alexa 488 and 647 dyes were coupled to the secondary antibodies using labeling kits (Lifetech #A20181 and A20186, respectively). The secondary antibodies were added to the lysate after 2 washes of the previous incubation, and were incubated at room temperature (20° C.) for 30 minutes with 2 additional washes following to remove unbound antibodies. Flow cytometry was performed on a BD FacsCantoII with 96-well, high-throughput capabilities. The counting of bead fluorescence occurrences, 'events', was set at 10,000-25,000 gated events setting from the previously published 2500 events (13). Note that 'gating' refers to the combination of fluorescence and scatter values that are counted.

Results

Figures 4A, 4B, 4C:
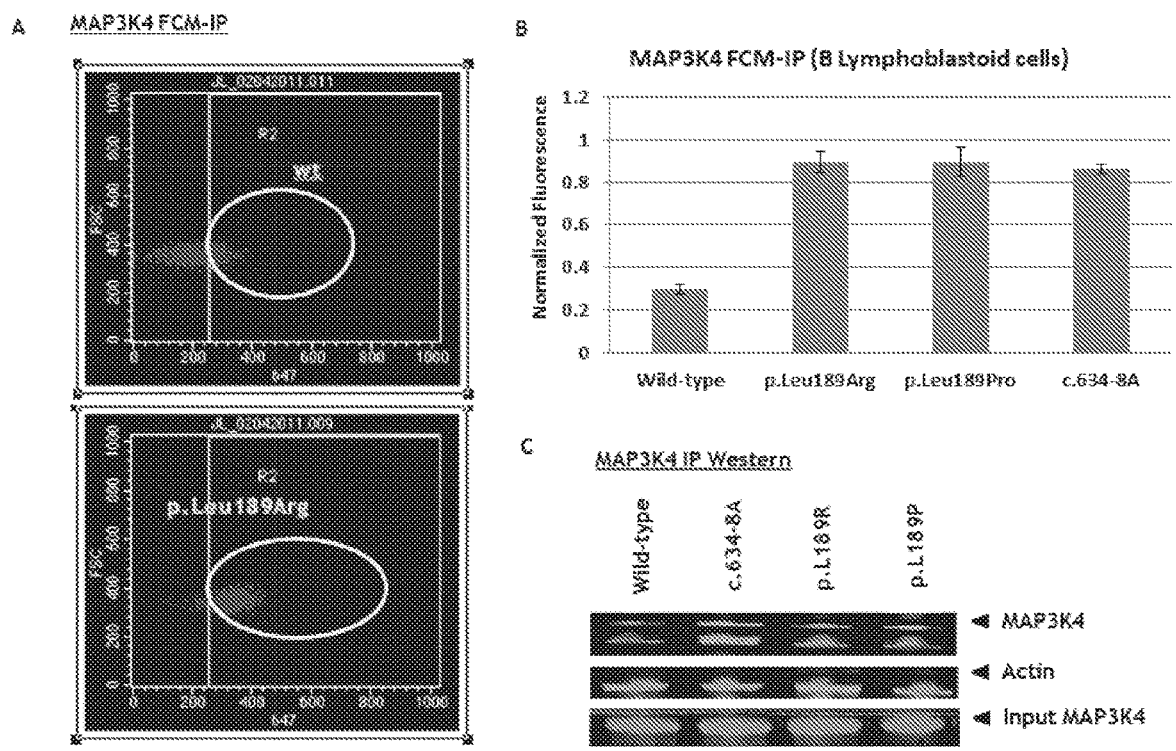
FIG. 4A-4C. Functional Variant Assay (FVA) performed on B-lymphoblastoid cells from wild-type and p.Leu189Arg using the MAP3K1 bait antibody and the Alexa 647 and Alexa 488-labeled MAP3K4 target antibodies. A. The flow cytometry gated results shows increased binding of MAP3K4 to mutant MAP3K1 as shown previously by standard methods. B. Results compiled from three independent experiments for each pathogenic mutation, Leu189Arg, p.Leu189Pro and c.634-8A show increased MAP3K4 binding to mutant MAP3K1 ($p<0.05$). C. Conventional IP Western blots of primary B-lymphoblastoid cells detected an approximate 2-fold increase of binding of MAP3K4 to MAP3K1 from all three mutant cell lines compared to wild-type. Loading control is actin and input control MAP3K1 on the lowest panel.
Figures 6A, 6B, 6C:
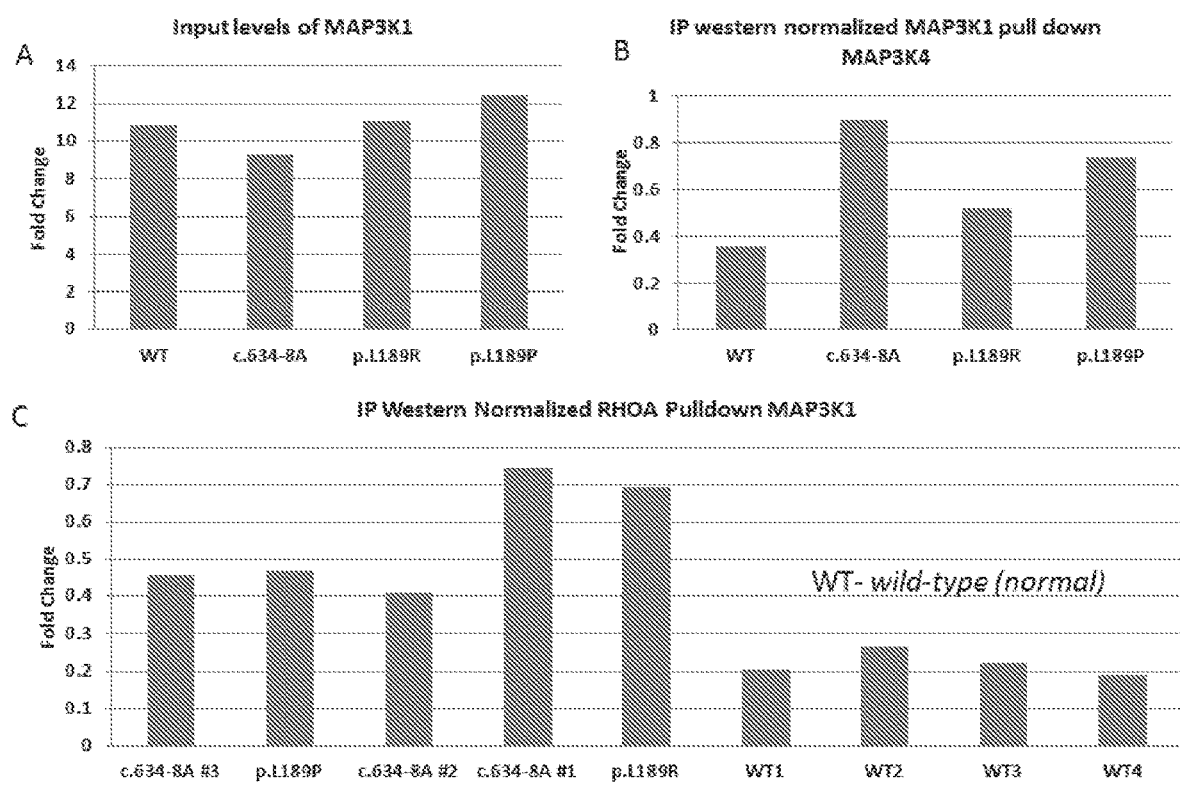
FIG. 6A-6C. A. Individual sample intensities of MAP3K1 input prior to pull-down for MAP3K4 for FIG. 4C were quantified from conventional Western blots using the Licor Software 3.0. B. After controlling for MAP3K1 loading the intensities were further normalized to actin, showing an average 2-fold increase of MAP3K4 binding in all mutant samples. C. Reverse IP using RHOA as bait shows increased binding of MAP3K1 to all mutant samples, about 2.5-fold increase compared to WT samples. These results were normalized to histone as a loading control.

The intrinsic fluorescence of the kit beads was low and did not interfere with subsequent analysis of binding fluorochromes. The fluorescence of the Alexa 488 and 647 dyes on antibody-conjugated epoxy beads was used, formulated using the kit coupling buffers (see protocol step 2 in "Preparation before starting") as reference control for calibrating the flow cytometer gate sensor to exclude background noise and to gauge dye detection and recognition fidelity. Positive controls from binding of either MAP3K1 or RHOA complexes to the beads could, in turn, be recognized by the labeled MAP3K1 and RHOA antibodies-demonstrating the specificity of these IP pull-down reactions. Western blot analysis was performed to confirmed that the expression of wild-type and mutant MAP3K1 proteins and that the input amounts of MAP3K1 prior to IP were consistent (FIGS. 4C and 6A). Previously, Western blot analysis showed that the input amounts of RHOA prior to IP were consistent (14). The IP Western from the MAP3K1 pull-down of MAP3K4, and the RHOA pulldown of MAP3K1 in the aggregate showed dramatic increases in binding among mutant samples as quantified by densitometry analysis using Licor Software 3.0 (FIGS. 6B and 6C). When applied to the analysis of the patient and control samples to measure protein interactions, the binding of MAP3K4 was shown by FVA to be increased 3-fold in these cell lines that contain any of three endogenous mutant MAP3K1 genes (C.654-8A, p.Leu189Pro and p.Leu189Arg) compared to wild-type cell lines (FIG. 4). The results observed with FVA were confirmed by conventional IP Western blots of samples eluted from the epoxy beads, although the binding appeared to be increased 2-fold on average among all mutants, similar results were observed in previous traditional IP Western. Accordingly, it was confirmed that the increases observed were not the result of unequal loading nor increased expression of MAP3K1, as illustrated by actin Western as loading control and MAP3K1 input prior to IP (FIG. 6B).

Figure 5A:
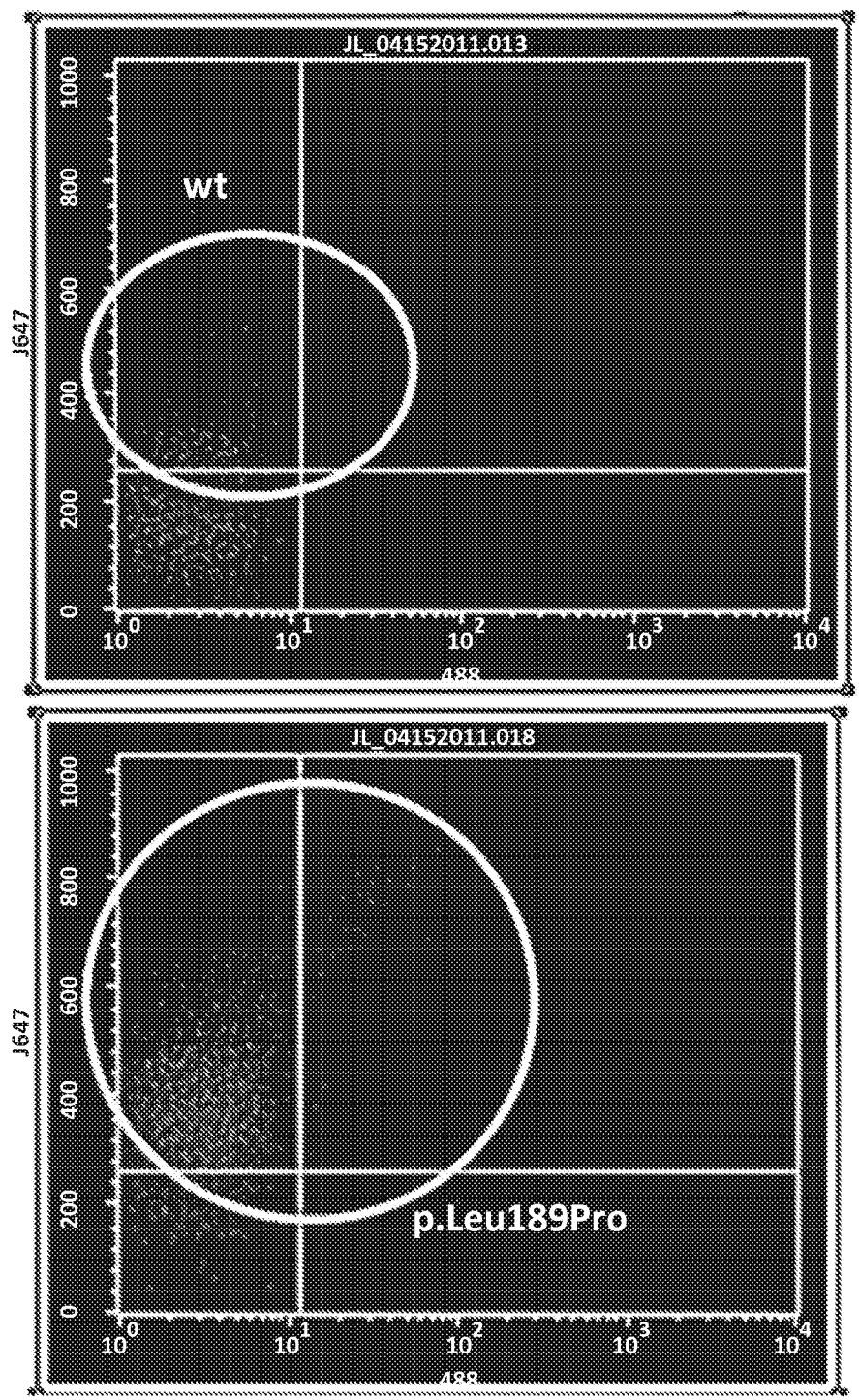

These methods were applied to the reverse immunoprecipitation method in which the 'bait' was RHOA, a MAP3K1-interacting protein to show consistency, and binding of wild-type or mutant MAP3K1 was measured by flow cytometry (FIG. 5). In this case, the binding of the mutant MAP3K1 proteins was increased 2 to 4-fold in cells containing mutant compared to wild-type MAP3K1. The results observed with FVA were confirmed consistent, and by conventional immunoprecipitation Western blots of samples eluted from the epoxy beads, notably the binding from all mutant cells appeared to be increased 2.5-fold compared to wild-type (FIGS. 5C and 6C). This discordance has been accounted for by the limited dynamic range of conventional Western blots compared to the sensitivity of flow cytometry.

Discussion

DNA sequencing of candidate genes or whole exomes on a diagnostic or investigational basis will yield a plethora of variants whose potential phenotypic roles cannot be readily demonstrated by prediction programs, SNP databases nor conventional genetic analysis. Many variants may produce phenotypic changes in the encoded proteins by affecting the quantity, post-translational modification or protein interactions. The present studies establish the application of the method of FVA to demonstrate that known protein interactions are altered in the B lymphoblastoid cells of patients with 46,XY gonadal dysgenesis arising from mutations in the MAP3K1 gene. This method can be scaled readily to test multiple interactions for many variants simultaneously from available tissues as well as quantify the effects of variants on protein accumulation and post-translational modification, thus functional screening of gene variants for phenotypic effects is made possible by this efficient and low-cost FVA.

Here, it was shown that the effects of missense and in-frame splicing (with insertion of 2 amino acids) mutations in the amino third of the MAP3K1 gene result in increased binding of MAP3K4. This might arise through interactions with their shared binding partner, AXIN1 (15-16). Both MAP kinases compete for AXIN binding, albeit at different sites (15), and the presence of these MAP3K1 mutations may alleviate this competition. Unlike MAP3K1, MAP3K4 is an essential testis determining gene. Homozygous loss of function alleles in mouse Map3k4 lead to disrupted testis development in mice from failure to support cord development (17), whereas knockout of the mouse Map3k1 gene does not (18). Reduction of MAP3K4 protein either from genetic knockout or from sequestration in MAP3K1-MAP3K4 complexes may have functionally similar effects. Increased binding of MAP3K4 to MAP3K1 complexes as shown by FVA may affect downstream WNT targets through AXIN1. AXIN1, an inhibitor of the WNT signaling pathway, interacts with β-catenin to reduce its protein abundance (16, 19). This results in an increase and/or stabilization of β-catenin, an effect that is known to cause male-to-female sex reversal in the XY gonad—in part by reducing SOX9 expression (20).

The present studies have also shown accurate detection of changes of binding partners to MAP3K1 in all three mutant MAP3K1 by FVA cases consistent with previous studies using traditional methods but at a higher fidelity (21).

These approaches of FVA, either with or without immunoprecipitation, can be applied to test other candidate gene variant expressions and functional implications. In the process, FVA can measure the general effects that a variant might have for a protein and its regulation of downstream targets. High-content measurements such as alteration of its expression and effects on the expression and accumulation of other downstream proteins in the cell, alteration of the post-translational modification of the variant protein, such as phosphorylation, or alteration of the variant and/or wild-type protein with its co-factors. Typically a handful of variants are selected for biological assays by genetic manipulation in cells or animals to show that a newly identified variant is a mutation, i.e. has a phenotypic effect. Previously, it has been shown that the effects on accumulation and post-translational modification can be measured reliably by flow cytometry in research and clinical applications (13, 27). The improved methods of FVA and kit presented here have been tested on human in-vitro studies using primary cells isolated from the subjects, and compared to standard genetic manipulated human cell lines to demonstrate for the use of FVA as high-throughput screening for the effects of genetic variants on binding of partners, at proteomic level (functional assay) that are readily adaptable for single-tube, 96- or 384-well approach. Thus, functional analysis of multiple variants and multiple binding partners in a single experiment in one or two days can be performed reliably and cost effectively. Moreover, comparison of previous IP-Western densitometry results with this invention FVA shows a greater sensitivity using only one-fifth the amount of starting material compared to traditional methods. The multiple binding partners can be tested in the same tube, because analytes using optically active antibodies each with different emission wavelengths can be measured simultaneously (27). Furthermore, the method can test not only interactions with binding partner, but also the quantification of the bound protein itself and its post-translationally modified forms, such as the phosphorylation status of the MAP kinase (28). The present methods and kits have been extensively tested in several other clinical genetic studies where B-lymphoblastoid cells isolated and immortalized from patients were used; these type of blood cells are commonly use in traditional genetic screening. As stated previously, the method was also tested in Neuronal Teratocarcinoma 2 (NT2) cells, a standard cell line routinely used in research laboratories to study gene variant effects by genetic manipulations.

In conclusion, this method proves to have clinical diagnostic value, a non-invasive, and cost effective test suitable for virtually any variants that are identified by massive parallel sequencing and genome-wide association studies (GWAS). In addition, the methods can be used to survey and identify the genetic heterogeneity of populations of cells. The methods can also be used to investigate epistatic interactions between proteins, wherein one protein is the distinct first protein of the method and the other protein is a distinct second protein.

Example B—Kits

Introduction

Protein expression is deemed to be a gold standard for measuring changes in gene activities. Many variants identified through sequencing or mutant characterization may produce phenotypic changes in the encoded proteins by affecting the quantity, post-translational modification or protein interactions. Indeed, the frequency of rare sequence variants is proving to be far higher than previously thought. Complex protein interactions play crucial roles in virtually all cellular processes. Traditionally, such protein-protein interactions were studied via co-immunoprecipitation. However, this method is laborious and are only useful for small number of targets, require large amount of biomaterial to start, not clinically sensitive and costly as each target must be measured independently in separate Western blots. Analysis of co-immunoprecipitation of protein complexes using FVA provides a sensitive rapid method to measure multiples of these interactions in their native state. This kit provides all the essential and optimized reagents to perform the assay along with a validated 'bait' antibody. First, target bait antibodies are covalently coupled to the bar-coded bead system in the kit. These antibody-coupled beads are used as bait for protein lysates. Finally, the pulled-down protein complexes on the beads are separated based on their properties and probed with optically active agent-labeled antibodies specific for interaction partners and measurement of a quantitative fluorescence are converted into quantity or numbers of co-binding molecules in a complex. FVA represents a robust technique to assess native protein-protein interactions rapidly with very small amount of biomaterials. This kit includes, for example but not limited to, seven optically active agents with minimal spectral overlap to measure multiple targets simultaneously with a standard three-laser flow cytometer, with methods that can be performed in just under one day, and alternative protocol allows for a two-day assay if needed.

Absolute Quantitative Flow Cytometry

Optical activity data are often presented on a relative scale with arbitrary units because it is inherently semi-quantitative by traditional means. This kit allows both measurements of semi and absolute quantification. This kit provides a set of standard optically active reference beads created using the same antibodies selected for each tests to generated standard curve, where optical activity values correspond to known numbers of molecules. Using this standard curve, on the same flow cytometer settings, absolute quantitation can be measured by translating the measured relative optical activity values from the FVA into numbers of target molecule per IP bead.

Kit Components

Kit components can include:

Immunoprecipitate Beads (Store at 4° C.)

Examples include, but are not limited to, polystyrene-epoxy paramagnetic (Dynabeads) beads (5 μM) in storage buffer, carboxylate-modified polystyrene surface latex (CML) beads (5 nm) in storage buffer, 10 ml of Flow grade neutral buffered salt solution, pH 7.4. Examples of buffers include Phosphate Buffered Saline, Phosphate Buffeted KCL, Trisaminomethane (Tris)-buffered ammonium chloride.

Coupling Buffers (Store at 25° C.)

Coupling buffers at pH range of 4-7 with use of agents, for example but not limited to, 2-[N-morpholino]ethanesulfonic acid (MES)) that allow covalent coupling of the agents on to the beads, chelating agents, for example but not limited to EDTA, and activating compounds, for example but not limited to 1-ethyl-3-(3-dimethylaminopropl) Carbodiimide HCl (EDAC) are added as well.

Fix-Permealization Buffer (DCW Buffer) (Store at 4° C.)

A kit for fix and permeabilizing cells comprising but not limited to (a) an isotonic or hypertonic fixing agent at pH 4 to 7 containing, for example but not limited to an aliphatic aldehyde or alcohol (glutaraldehyde, para- or formaldehyde, alcohol), which is present in a concentration of at least 5%, (b) a permeabilizing agent, for example but not limited to at pH 4 to 8 containing a blocking agent (Bovine serum albumin, BSA) and selected group consisting of Zwitterionic and the use of ionic detergent (e.g., Sodium dodecyl sulfate, SDS).

Inhibitor Cocktail (Store at −20° C.)

Phosphatase Inhibitor Cocktail

A kit containing phosphatase inhibitor that inhibits phosphatases. Examples of phosphatase inhibitors than can be used include, but are not limited to, sodium orthovanadate and sodium fluoride, and contain a preservative such as Sodium Azide.

Proteinase K Inhibitor Cocktail

A kit containing Proteinase K inhibitor that inhibits Proteinase Ks including for example but not limited to chymotrypsin, kallikrein, plasmin, thrombin, and trypsin. Examples of inhibitors include, but are not limited to, phenylmethanesulfonyl fluoride (PMSF) or 4-(2-Aminoethyl)benzenesulfonyl fluoride (AEBSF), and contain a preservative such as Sodium Azide.

Universal Buffer (Blocking and Storage)

A buffer containing, for example but not limited to, blocking agent (BSA), host serums (Rabbit, mouse, and/or goat serum), preservative (Sodium Azide). Formulations include isotonic and hypertonic saline, buffering agent and salts, examples include but not limited to Phosphate buffer saline (PBS), Potassium chloride (KCL), Monopotassium phosphate ($KH_2PO_4$), Sodium chloride (NaCl), Disodium hydrogen phosphate (Na2HPO4) and Tris.

After-IP Buffer

A buffer containing, for example but not limited to, Proteinase K inhibitors (PMSF or AEBSF), preservative (Sodium Azide), isotonic and hypertonic saline, buffering salts, examples include but not limited to Sodium chloride (NaCl).

FVA Buffer

A buffer containing, for example but not limited to, blocking agent (BSA), host serums (Rabbit, mouse, and/or goat serum), preservative (Sodium Azide), isotonic and hypertonic saline, buffering agent and salts, examples include but not limited to Phosphate buffer saline (PBS), Potassium chloride (KCL) or Sodium chloride (NaCl) and Tris.

Lysis Buffer

A buffer containing, for example but not limited to, a buffering agent (Tris), Proteinase K inhibitors (PMSF or AEBSF), phosphatase inhibitors (Sodium Orthovanadate, Sodium Fluoride), a chelating agent (EDTA), contains hypertonic salt, examples include but not limited to Potassium chloride (KCL) and/or Sodium chloride (NaCl), non-ionic detergent (Digitonin) or ionic detergent (SDS).

Elution Buffer (Store at 4° C.)

A buffer containing, for example but not limited to, blocking agent (BSA), Proteinase K inhibitors (PMSF or AEBSF), phosphatase inhibitors (Sodium Orthovanadate, Sodium Fluoride), a chelating agent (EDTA), a preservative (Sodium Azide), contains hypertonic salt, examples include but not limited to Potassium chloride (KCL) and/or Sodium chloride (NaCl), a buffering agent (Trisaminomethane (Tris)), non-ionic detergent (Digitonin) or ionic detergent (SDS, or Triton X-100).

Nuclear Enrichment Buffer (Store at 4° C.)

To remove the cytoplasmic compartment of the cells with or without fixation (DCW buffer), resuspend cell pellet in NP40 with Tween 20 lysis buffer: 30 mM Tris/Hepes, pH 8.0, (0-50 mM) NaCl, 3 mM EDTA, 1.5 mM phenylmethylsulfonyl, fluoride (PMSF or equivalent agent), 1% Tween 20 and 1% NP40. Leave on ice for 15 min with pipetting for 5 times, then pellet the nuclei at 2000-6000 g for 3 min at +4° C. Collect or decant the supernatant (cytoplasm fraction) supplemented with 300 mM NaCl if needed for FVA analysis. Resuspend the nuclear pellet in 100 ul of Universal buffer containing host IgG and store 24 hours in 4° C. prior to assay, add 120 ul of methanol if long term storage is desired.

Western Loading Buffer

A buffer containing, for example but not limited to, ionic detergent (SDS, or Triton X-100), a buffering agent (Tris), coloring agent (Bromophenol blue), a hygroscopic simple polyol compound (glycerol) and a small-molecule redox reagent such as Cleland's reagent, example include but not limited to Dithiothreitol (DTT) or dithioerythritol (DTE).

Nucleic Acids Recovery Elution Buffer Mix

A buffer containing, for example but not limited to, protein digesting agent (proteinase K), a chelating agent (EDTA), isotonic and hypertonic saline, detergent buffering agent and salts, examples include but not limited to Phosphate buffer saline (PBS), Potassium chloride (KCL), potassium phosphate ($KHPO_4$), Calcium chloride (CaCl), Glycine, Tris.

Protease Inhibitor Cocktail

A buffer containing, for example but not limited to, proteinase inhibitors PMSF and Diisopropyl phosphorofluoridate (DPF)) and a chelating agent (Ethylene glycol tetraacetic acid, (EGTA)).

Preparation Before Starting

Coupling of Bait Antibodies to Beads.

Pipette 20 µL (18×10⁶) Dynabeads into a 1.5-mL microcentrifuge tube. Wash the beads 2 times in 700 µL Buffer Ca, magnetize the tube and remove supernatant after each wash. Then, resuspend the bead pellet in 25 µL Buffer C1; then transfer all into provided C2 tube (to activate the coupling group on the beads). Mix gently on an orbital shaker for 15 min at room temperature (25° C.). Repeat with CML beads.

Wash the activated beads 2 times in 700 µL Flow PBS, magnetize the tube and remove supernatant after each wash. Resuspend the activated beads in 50 µL Flow PBS. Add 50 µL of the bait antibody (0.2-1.0 mg/mL stock concentration) to the activated bead mix. Mix for 2 hours at 25° C. by placing the tube on a vibrating shaker or taped to a standard vortexer at low shake setting. This will ensure sufficient mixing to prevent settling of the beads. Overnight incubation is not necessary as this kit is optimized for rapid coupling.

Wash Ab coupled beads 2 times in 700 µL PBS, magnetize the tube for Dynabeads, and remove supernatant after each wash. Place the CML beads for 5 minutes of centrifugation at 5000 g. Resuspend the coupled beads in 100 µL Universal Buffer. These can be stored at 4° C. for at least one year. Resuspend the beads well before use to ensure consistency for each experiment.

Optically Active Agent Labeling on Antibodies and Optical Reference Control preparation.

Up to 150 µg of antibody per reaction can be set up in the provided glass vials. Antibody to dye ratio is 1:1. Total reaction volume optimally should be at 110 µL finally.

1) Add 10 µL Modifier into the 100 µL of antibodies, mix gently.

2) Pipette all the mix into the lyophilized dye in the glass vial, mix and incubate for 3 hours to overnight in dark at room temperature, 25° C.

3) Add 1 µL of quencher for every 10 µL antibody used. The conjugate can be used after 30 minutes of quenching. For optical reference control preparation, follow the entire step of "Coupling of bait antibodies to beads" with the conjugated antibodies.

Performing Digital-Cell Western (DCW).

Count, and pellet $1 \times 10^6$ cells for each sample to perform DCW. 16% formaldehyde is added directly into the culture medium, please note final formaldehyde concentration should be at 1.5% and incubated the cells for 10 min at 25° C. or room temperature (RT). Then, pellet the cells (use dissociation media for adherent cells) by low speed centrifugation. Resuspend the cell pellet by vortexing in 500 µl ice-cold Methanol and incubated on ice for 5 minutes. Cells can be stored at −80° C. for long term with minimum degradation.

To perform staining for target protein expression, cells should be washed twice in 500 µl cold Universal buffer then resuspended with this buffer at 50 µl. It is recommended to test fidelity of antibodies, but standard guidelines is approximately 50 ng of optically active labeled antibodies should be added and incubated for 30 min at 4° C. Then wash the cells twice with 500 µl cold Universal buffer. Finally, samples were resuspended in 150 µl FVA Buffer and analyzed by flow cytometer (as noted in Performing FVA Scan)

Performing FVA Complex Capture.

While lysis method and optimal lysis conditions can vary in some cases of transient protein-protein interactions being investigated, the lysis buffer provided in this kit is designed to meet most applications and is suitable in many cases. Each lysis buffer is sufficient to perform 10 IPs, and contain most necessary inhibitors. Alternatively, other lysis buffers in general are compatible to be used with this kit.

Lysis of $30 \times 10^6$ cells in 100 µL fresh Lysis buffer in a 1.5-mL microcentrifuge tube for 10-20 minutes on ice. Scale the lysis volume as needed. Two sonication pulses into the lysate are highly recommended for most applications. Cell debris and nuclei can be removed by brief centrifuge of the lysate at 5000 g for 2 minutes at 4° C. Keep the supernatant and discard the pellet. Add $1 \times 10^5$ of the coupled beads to the lysate, (recommend using chimney-bottom 96 well plate for this step). Use 50 µL of the lysate to perform FVA for each sample. The lowest volume can be at 5 µL. Place on a vertical rotating wheel 4 hours in a cold room, alternatively, overnight incubation in cold room can be performed. Ensure proper mixing to prevent bead settling.

Probing of Bead-Captured Protein with Optically Active-Labeled Antibodies.

Wash the IP beads two times in 500 µL ice-cold FVA Buffer, magnetize and remove supernatant and transfer it into a second vessel (tubes or plates). Centrifuge for 5 minutes at 5000 g, and remove supernatant, the pellet is the CML-analyte complex, and perform two washes for Dynabeads and CML beads, magnetize and centrifuge respectively and discard supernatant after each wash. Resuspend the beads in 20 µL FVA buffer. Add optically active-labeled antibodies to the samples. Check with vendor's recommendation on antibody concentration use. In most applications, add 0.5 µL of stock antibody solution (at 0.2-1.0 mg/mL) per tube or well, and incubate for 35 minutes on ice on an orbital shaker. Wash probed samples two times in 500 µL ice-cold FVA buffer, magnetize and remove supernatant after each wash. Resuspend the beads in 200 µL FVA buffer per sample. Samples are now ready for FVA scan and analysis.

Performing FVA Scan

The supplied beads in this kit are about 5 µm in diameter, approximately half the diameter of a typical lymphocyte. Set forward Scatter (FSC) amp gain to 480 and the side scatter (SSC) voltage to 550 to register the population of bead events to on scale. Both Dynabeads and CML beads should form distinct clusters/population in a linear fashion, place the gate circle on all distinct populations of beads. The settings and gate should be adjusted to include only beads populations not cell debris which are typically seen below the bead populations.

Use the default collection criterion, which for most applications is 10,000-25,000 acquisition events. Adjustment of this criterion to higher acquisition events may be needed for rare target. The staining of the beads normally produces distinct mode fluorescence intensity (MoFI) when visualized on a histogram mode, change to Standard "log mode" for the use in fluorescence channel(s) detection.

Prepare and use unlabeled, unconjugated beads as the first sample to set the negative control photomultiplier tube (PMT) voltage. Optionally, bright positive control for the second sample, such as beads with optically active-conjugated antibodies (See Preparation before starting). Initially, a run of internal optical standards is necessary, for each flow cytometer used. This will create a spectral compensation profile that can be used for subsequent and future FVA scans. The flow cytometer is now ready to acquire the FVA from the probed samples.

Performing Protein-Nucleic Acid Enrichment

Upon completion of flow sorting, population of beads can be precipitated by applying magnetic field for Dynabeads and transfer the supernatant to a new tube or plate and centrifuge at 5000 g for 5 minutes to pellet the CML beads then discard the supernatant. No wash needed. Heat the beads to 90° C. for 15 minutes, cool on ice for 5 minutes then add 50 µL of 1× Nucleic acids recovery buffer mix to the captured beads and incubate at 55° C. for 2 hour. Apply magnetic field on the Dynabeads digested mix and centrifuge at 5000 g for the CML digested mix, and transfer the supernatant into respective new tubes/plates. Add 5 µL of 10× Proteinase inhibitor to the supernatant. Optionally, standard DNA purification can be performed after this step but the supernatant is suitable for direct use in applications of MPS, allelic discrimination assays, quantitative PCR expression analysis, and RNA/CHIP PCR assays.

Example C—Nuclear Assay—Localization

Figure 7A:
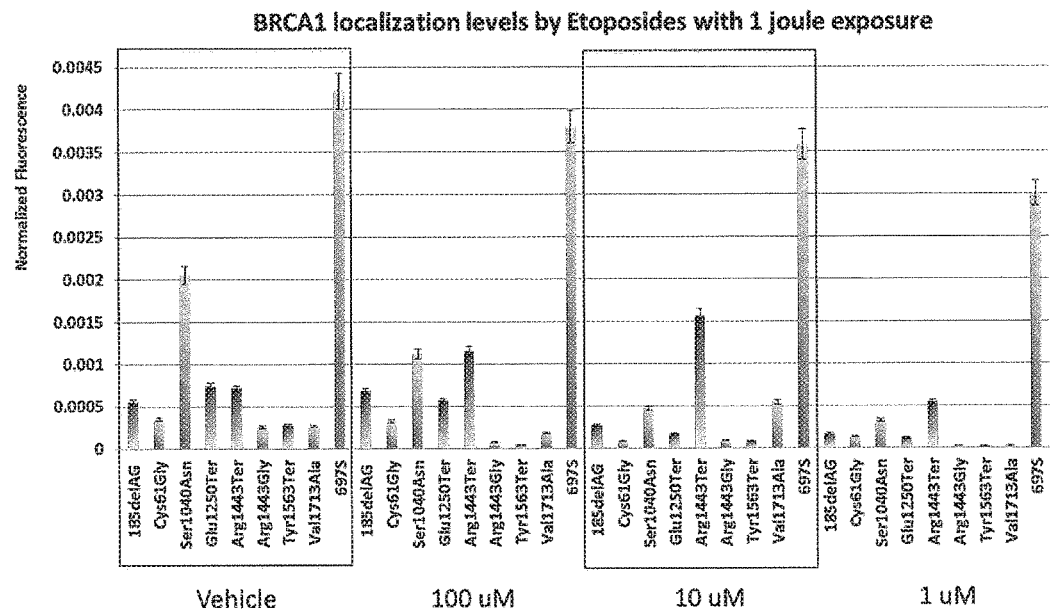
FIG. 7A-7B. A. After treatment with Etoposide and UV radiation or B. the X-Ray mimetic drug, Bleomycin, the localization of BRCA 1 to nuclear foci was markedly lower among mutant samples compared to normal samples as measured with the present assay.
Figure 7B:
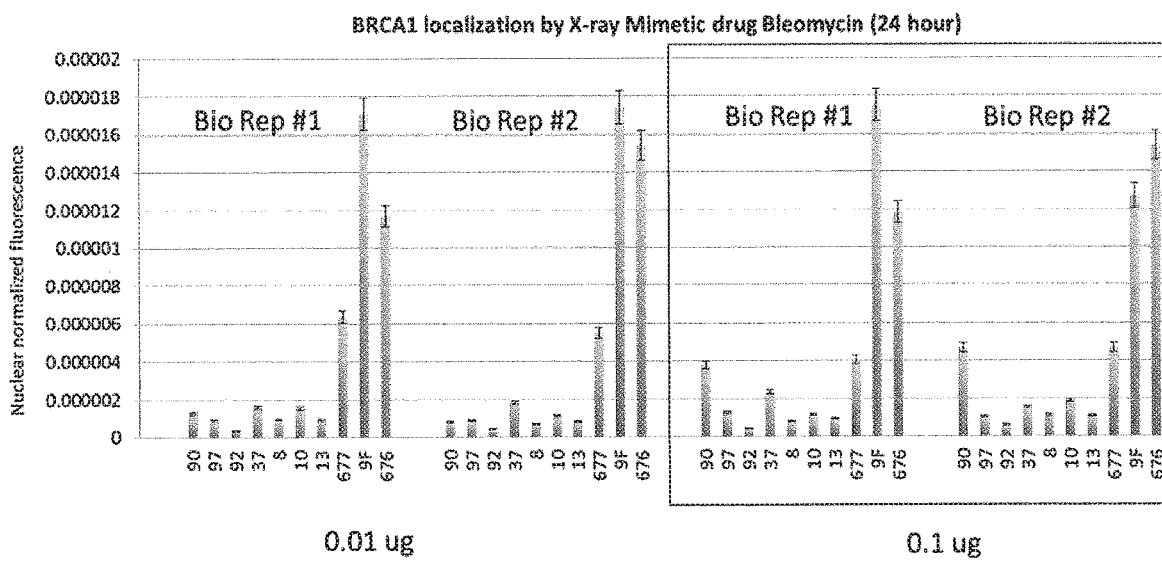
Figure 8:
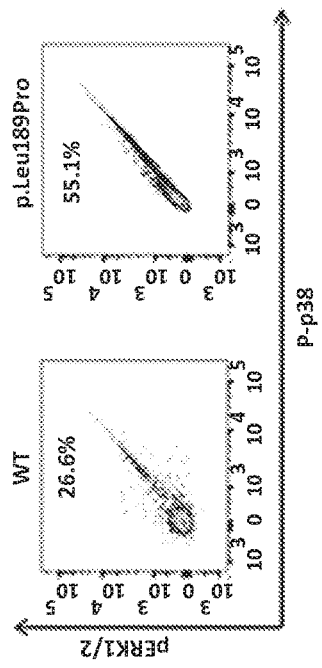
FIG. 8. Traditional phospho-Western vs. Digital Cell phospho-Western. Preparation and run: 2 days vs. less than 2 hours. Traditional IP-western vs. Flow Variant Analysis: Preparation and run time: 5 days vs. 5 hours.
Figure 8:
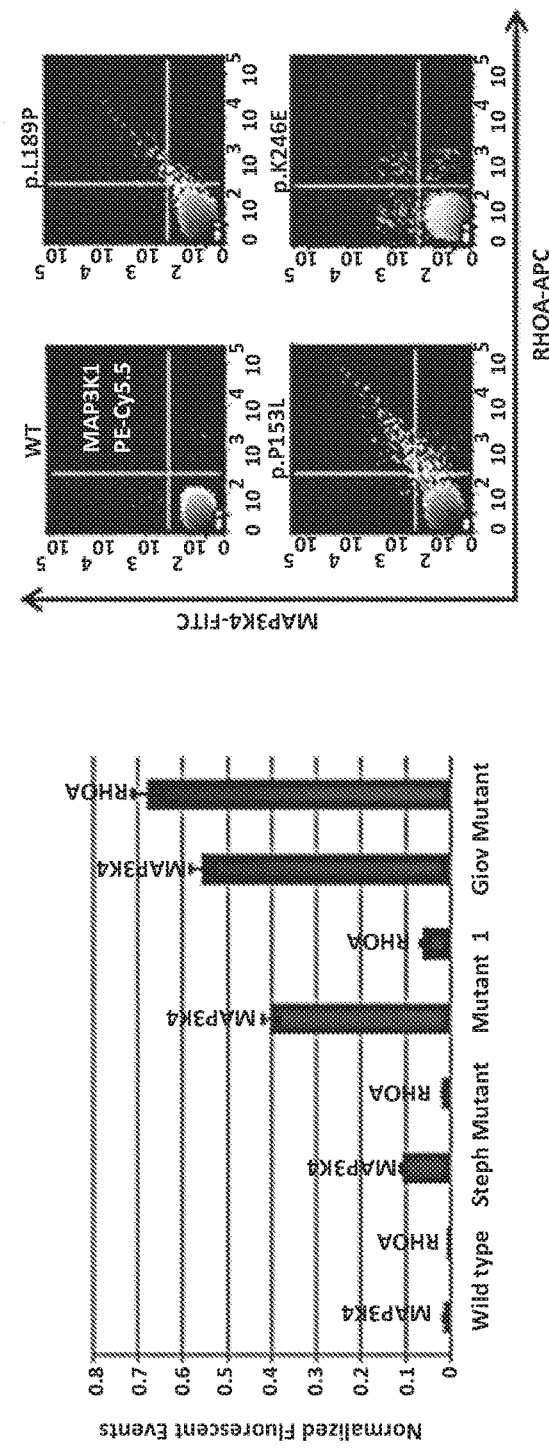

BRCA1 expression and localization were analyzed in isolated primary B-Lymphoblastoid cells from individuals with BRCA1 mutations. The assays were performed as randomized, anonymized samples. The cells were treated with Etoposide and UV radiation to cause double-stranded DNA breaks. About 2 million cells were formalin-fixed and methanol permealized. Each experiment included three biological and three technical repeats. The cytoplasmic fraction was removed by hypotonic salt lysis method followed by nucleus enrichment by centrifugation. Flow staining hydration buffer was used overnight at 4° C. to increase the nucleus ball diameter from 2-3 μm to above 5-7 μm, followed by nuclear staining with optically-labeled primary antibodies. The results demonstrated that after treatment with Etoposide and UV radiation (FIG. 7(A)) or the X-Ray mimetic drug, Bleomycin (FIG. 7(B)), the localization of BRCA1 to nuclear foci was markedly lower among mutant samples compared to normal samples. The samples were compared to IgG (i.e., negative) controls The bead internal autofluorescence and selected size events were also compared. The BRCA1 relative fluorescence intensity was normalized by dividing with the specific events to the total gated events. An inverse correlation (P<0.0001) was observed between BRCA1 localization/staining in the nuclear/pathogenicity upon DNA damage drug treatment. All cell lines with mutations showed significantly lower staining, whereas normal cell lines demonstrated strong nuclear staining. The staining intensity denotes BRCA1 localization into the nucleus for DNA double stranded repair (DSB). The mutations in BRCA1 abrogated this localization and repair mechanism.

The nuclear localization kit, and method herein, have been developed for the preparation of enrichment of nuclear, whole-cell and cytoplasmic extracts from cells or tissue. This kit provides method that is simple, fast and effective to measure protein activities within cytoplasmic and/or nuclear compartments of the cell. The nuclear localization kit can be used to prepare intact nuclear balls (cellular nuclei) to monitor tumor suppressor genes activities in whole intact cell and intact cellular nucleus. The nuclear compartment enrichment collected by this kit can be used for a variety of standard protocols besides PrCo-IP, NACo-IP, FVA, including electrophoretic mobility shift assay (EMSA), DNA footprinting, Western blotting and preparative purification of nuclear proteins.

Each kit provides reagents for direct lysis of cells. First, the cells are collected in ice-cold PBS in the presence of phosphatase inhibitors or fixation (e.g. by 2% paraformaldehyde) to limit further protein modifications (expression, proteolysis, dephosphorylation, etc.). Then, the cells are resuspended in hypotonic lysis buffer and strong detergent added which causes breakage of the cells resulting in leakage of cytoplasmic proteins into the supernatant. After collection of the cytoplasmic fraction, the nuclei are fixed-permeabilized with, e.g., a methanol-based storage buffer.

To prepare whole-cell extracts, cells are collected in the PBS/phosphatase Inhibitors solution and lysed in the lysis buffer. Solubilized proteins are separated from the cell debris by centrifugation. The protein concentration of the cell extract can be normalized by counting number of live cells during cell collection, no protein quantification necessary. Optionally, a Bradford assay can be used at this step. The method or kit can be used to obtain nuclear, cytoplasmic or whole-cell extract from cells or from tissue.

Successful extraction has been performed with NT2/D1, PC3, LNCaP, DU145, and B-lymphoblastoid cells. In an embodiment, the kit used comprises the components as follows:
Lysis Buffer AM1 (e.g. 10 ml)
1 M Dithiothreitol (DTT) (e.g. 500 μl)
Protease Inhibitor mix (e.g. 500 μl)
10×PBS (e.g. 4×100 ml)
Phosphatase Inhibitors (e.g. 4×50 ml)
10× Hypotonic Buffer (e.g. 50 ml)
Detergent (NP40 mix) (e.g. 5 ml).
Protocol Examples:

The following exemplary protocol is based on samples of approximately $20 \times 10^6$ cells, which corresponds to 10 wells on a 96-well plate. Each well is one reaction. Prepare PBS/phosphatase inhibitors, hypotonic buffer and total lysis buffer. Place buffers and any tubes needed on ice before beginning assay.

Step 1: Cell Collection
1. Aspirate media out of culture vessel. Wash with 5 ml ice-cold PBS/Phosphatase Inhibitors. Aspirate solution out and add 3 ml ice-cold PBS/Phosphatase Inhibitors.
2. Remove cells from flask/dish by gently scraping with cell lifter for adherent cells. Transfer cells to a sterile 50 ml conical tube.
3. Centrifuge cell suspension for 5 minutes at 500 rpm in a centrifuge pre-cooled at 4° C.
4. Discard supernatant. Keep cell pellet on ice.

Step 2: Cytoplasmic Fraction Collection
1. Gently resuspend cells in 5 ml 1× Hypotonic Buffer with 250 μl NP40 detergent by pipetting up and down several times. Transfer to a pre-chilled microcentrifuge tube. Incubate for 15 minutes on ice.
2. Vortex 10 seconds at highest setting.
3. Centrifuge suspension for 30 seconds at 2-3,000×g in a centrifuge pre-cooled at 4° C.
4. Transfer supernatant (cytoplasmic fraction) into a pre-chilled microcentrifuge tube. (If you began working from tissue, combine this supernatant with that obtained in Step 1, No. 3 of the Nuclear enrichment protocol for tissue.) Store the supernatant at −80° C. until ready to use. Use the pellet for nuclear collection.

Step 3: Nuclear Enrichment Collection and Nuclear Extracts.
1. Resuspend nuclear pellet in fixation and permeabilizing buffer or 500 μl Total lysis buffer by pipetting up and down. Vortex 10 seconds at highest setting.
2. Incubate suspension for 30 minutes on ice on a rocking platform set at 150 rpm.
3. Vortex 30 seconds at highest setting. Centrifuge for 10 minutes at 14,000×g in a microcentrifuge pre-cooled at 4° C. Transfer supernatant (nuclear fraction) into a pre-chilled microcentrifuge tube.
4. Aliquot and store at −80° C. Avoid freeze/thaw cycles.

Starting from Tissue:
Step 1: Tissue Homogenization
1. Weigh tissue and dice into very small pieces using a clean razor blade. Collect pieces in a pre-chilled, clean MP homogenizer Fastprep 24 sample prep tubes (6900 series).
2. On ice, add 3 ml ice-cold IX hypotonic buffer supplemented with DTT and Detergent (3 μl of the provided 1 M DTT and 3 μl of the provided detergent) per gram of tissue and homogenize. Incubate on ice for 15 minutes.
3. Centrifuge for 10 minutes at 850 x g at 4° C. Transfer the supernatant into a prechilled microcentrifuge tube. (Save this supernatant and pool it with the supernatant that will be collected later in Step 2, No. 3 of the Nuclear enrichment protocol for cells.)
4. At this point, the tissue is homogenized. However, most of the cells are not yet lysed. Therefore, continue the procedure with the cell pellet at Step 2, No. 1 of the Nuclear enrichment protocol for cells, based on a 20×106 cells.

REFERENCES

1. Ostrer H. Changing the game with whole exome sequencing. Clin Genet 2011: 80: 101-3.

2. Pelak K, Shianna K V, Ge D et al. The characterization of twenty sequenced human genomes. PLoS genetics 2010: 6.
3. Ng S B, Turner E H, Robertson P D et al. Targeted capture and massively parallel sequencing of 12 human exomes. Nature 2009: 461: 272-276.
4. Sherry S T, Ward M H, Kholodov M et al. dbSNP: the NCBI database of genetic variation. Nucleic Acids Res 2001: 29: 308-311.
5. Reese M G, Eeckman F H, Kulp D et al. Improved splice site detection in Genie. Journal of computational biology: a journal of computational molecular cell biology 1997: 4: 311-323.
6. Ng P C, Henikoff S. SIFT: Predicting amino acid changes that affect protein function. Nucleic Acids Res 2003: 31: 3812-3814.
7. Bromberg Y, Yachdav G, Rost B. SNAP predicts effect of mutations on protein function. Bioinformatics 2008: 24: 2397-2398.
8. Adzhubei I A, Schmidt S, Peshkin L et al. A method and server for predicting damaging missense mutations. Nature methods 2010: 7: 248-249.
9. Cooper D N, Krawczak M. The mutational spectrum of single base-pair substitutions causing human genetic disease: patterns and predictions. Hum Genet 1990: 85: 55-74.
10. Hartwell L H, Hopfield J J, Leibler S et al. From molecular to modular cell biology. Nature 1999: 402: C47-52.
11. Wu A H. A selected history and future of immunoassay development and applications in clinical chemistry. Clinica chimica acta; international journal of clinical chemistry 2006: 369: 119-124.
12. Identification of associated proteins by coimmunoprecipitation. Nature methods 2005: 2: 475-476.
13. Schrum A G. Visualization of multiprotein complexes by flow cytometry. Current protocols in immunology/edited by John E Coligan [et al] 2009: Chapter 5: Unit5 9.
14. Pearlman A, Loke J, Le Caignec C et al. Mutations in MAP3K1 cause 46,XY disorders of sex development and implicate a common signal transduction pathway in human testis determination. Am J Hum Genet 2010: 87: 898-904.
15. Luo W, Ng W W, Jin L H et al. AXIN utilizes distinct regions for competitive MEKK1 and MEKK4 binding and JNK activation. J Biol Chem 2003: 278: 37451-37458.
16. Sue Ng S, Mahmoudi T, Li V S et al. MAP3K1 functionally interacts with AXIN1 in the canonical Wnt signalling pathway. Biol Chem 2010: 391: 171-180.
17. Bogani D, Siggers P, Brixey R et al. Loss of mitogen-activated protein kinase kinase kinase 4 (MAP3K4) reveals a requirement for MAPK signalling in mouse sex determination. PLoS Biol 2009: 7: e1000196.
18. Warr N, Bogani D, Siggers P et al. Minor abnormalities of testis development in mice lacking the gene encoding the MAPK signalling component, MAP3K1. PLoS One 2011: 6: e19572.
19. Nakamura T, Hamada F, Ishidate T et al. AXIN, an inhibitor of the Wnt signaling pathway, interacts with beta-catenin, GSK-3beta and APC and reduces the beta-catenin level. Genes Cells 1998: 3: 395-403.
20. Maatouk D M, DiNapoli L, Alvers A et al. Stabilization of beta-catenin in XY gonads causes male-to-female sex-reversal. Hum Mol Genet 2008: 17: 2949-2955.
21. Gallagher E D, Gutowski S, Sternweis P C et al. RhoA binds to the amino terminus of MEKK1 and regulates its kinase activity. J Biol Chem 2004: 279: 1872-1877.
22. Tew S R, Hardingham T E. Regulation of SOX9 mRNA in human articular chondrocytes involving p38 MAPK activation and mRNA stabilization. J Biol Chem 2006: 281: 39471-9.
23. Woods A, Wang G, Beier F. RhoA/ROCK signaling regulates Sox9 expression and actin organization during chondrogenesis. J Biol Chem 2005: 280: 11626-11634.
24. Kumar D, Lassar A B. The transcriptional activity of Sox9 in chondrocytes is regulated by RhoA signaling and actin polymerization. Mol Cell Biol 2009: 29: 4262-4273.
25. Murakami S, Kan M, McKeehan W L et al. Up-regulation of the chondrogenic Sox9 gene by fibroblast growth factors is mediated by the mitogen-activated protein kinase pathway. Proc Natl Acad Sci USA 2000: 97: 1113-1118.
26. Cool J, Capel B. Mixed signals: development of the testis. Semin Reprod Med 2009: 27: 5-13.
27. Deswal S, Schulze A K, Hofer T et al. Quantitative analysis of protein phosphorylations and interactions by multi-colour IP-FCM as an input for kinetic modelling of signaling networks. PLoS one 2011: 6: e22928.
28. Chow S, Patel H, Hedley D W. Measurement of MAP kinase activation by flow cytometry using phospho-specific antibodies to MEK and ERK: potential for pharmacodynamics monitoring of signal transduction inhibitors. Cytometry 2001: 46: 72-78.

What is claimed is:

1. A method of analyzing genetic pathways comprising the following steps in the recited order:
   (a) providing a control and an experimental group of cells, wherein the control group of cells express at least four distinct wild type primary proteins, primary proteins A, B, C and D respectively, and wherein the experimental group of cells express variants of primary proteins A, B, C and D, wherein the variants have at least 97% or greater but less than 100% sequence identity with the primary proteins;
   (b) lysing the control and the experimental group of cells;
   (c) contacting each cell lysate in parallel with (i) a first primary agent attached to a surface of a magnetic bead that is not conjugated to an optically-active label, wherein the first primary agent is a binding partner capable of capturing the first protein A or the variant of primary protein A, (ii) a second primary agent attached to a surface of a magnetic bead that is conjugated to a first optically-active label, (iii) a third primary agent attached to a surface of a non-magnetic bead that is not conjugated to an optically-active label, and (iv) a fourth primary agent attached to the surface of a non-magnetic bead that is conjugated to a second primary optically-active label, wherein the second, third and fourth primary agents are different binding partners each capable of capturing the distinct primary proteins B, C, and D, or variants of primary proteins B, C, and D, respectively;
   (d) contacting the protein-captured beads with (i) a first secondary optically-active label conjugated with a secondary agent, a binding partner that is capable of interacting with a first secondary protein, (ii) a second secondary optically-active label conjugated with a secondary agent that is capable of interacting with a second secondary protein, (iii) a third secondary optically-active label conjugated with a secondary agent that is capable of interacting with a third secondary protein, and (iv) a fourth secondary optically-active label conjugated with a secondary agent that is capable of interacting with a fourth secondary protein, wherein the second, third and fourth secondary agents are different binding partners each capable of interacting with a distinct secondary protein;

(e) passing the beads through a flow cytometer or optical plate reader;

(f) adjusting the forward scatter amplitude gain and side scatter voltage on a flow cytometer with a control un-complexed bead population prior to initiating the method of detecting complexed beads;

(g) detecting each optical signal of each bead, wherein each optical signal represents data from a single bead;

(h) aggregating each optical signal from each bead that have bound primary proteins A, B, C and D and variants of primary proteins A, B, C and D to identify the binding of primary proteins A, B, C and D and variants of primary proteins A, B, C and D;

(i) aggregating each optical signal from each bead and assessing the expression levels of the secondary proteins, wherein the aggregated optical signal from the first secondary optically-active label is used to identify the binding of the first secondary protein, the aggregated optical signal from the second secondary optically-active label is used to identify the binding of the second secondary protein, the aggregated optical signal from the third secondary optically-active label is used to identify the binding of the third secondary protein, and the aggregated optical signal from the fourth secondary optically-active label is used to identify the binding of the fourth secondary protein;

(j) recovering magnetic bead complexes by applying a magnetic field;

(k) recovering non-magnetic bead complexes;

(l) passing the recovered magnetic bead complexes through a flow cytometer or optical plate reader;

(m) passing the recovered non-magnetic bead complexes through a flow cytometer or optical plate reader;

(n) detecting the optical signal(s) of the recovered magnetic bead complexes; and (o) detecting the optical signal(s) of the recovered non-magnetic bead complexes (p) determining protein-protein interactions between the primary proteins A, B, C, and D or the variants of primary proteins A, B, C, and D, and the secondary proteins;

wherein the presence on a magnetic bead complex of only a secondary optically-active label indicates the interaction between the primary protein A or the variant of primary protein A and a second protein corresponding to the secondary optically-active labeled secondary agent;

and wherein the presence on a magnetic bead complex of both (i) a first primary optically-active label and (ii) a secondary optically-active label indicates the interaction of the first protein B or the variant of primary protein B and a second protein corresponding to the secondary optically-active labeled secondary agent;

and wherein the presence on a non-magnetic bead complex of only a secondary optically-active label indicates the interaction of the first protein C or the variant of primary protein C and a second protein corresponding to the secondary optically-active secondary labeled agent;

and wherein the presence of a non-magnetic bead complex of both (i) a second primary optically-active label and (ii) a secondary optically-active label indicates the interaction of the first protein D or the variant of primary protein D and a second protein corresponding to the secondary optically-active labeled secondary agent; and (q) comparing the protein-protein interactions detected from the control group of cells with the protein-protein interactions detected from the experimental group of cells, thereby determining whether the experimental group of cells has any functional variation in the variants of primary proteins A, B, C or D as compared to the control group of cells.

2. The method of claim 1, wherein recovering non-magnetic bead complexes in step (j) is achieved by centrifugation.

3. The method of claim 1, wherein each primary agent comprises an antibody or comprises an antigen-binding fragment of an antibody.

4. The method of claim 1, wherein each secondary agent comprises an antibody or comprises an antigen-binding fragment of an antibody.

5. The method of claim 3, wherein the antibodies are monoclonal or polyclonal antibodies.

6. The method of claim 3, wherein the antibody fragments are F(ab')2 fragments, Fab' fragments or ScFvs.

7. The method of claim 1, wherein the magnetic beads are epoxy-coated magnetic beads.

8. The method of claim 1, wherein the non-magnetic beads are carboxyl modified beads.

9. The method of claim 1, wherein forward scatter amplitude gain and side scatter voltage on a flow cytometer are set to register populations of bead events to on scale, followed by applying an inclusion gate where selected linear populations of beads form collective clusters containing interrogation targets and can be analyzed in their entirety by flow cytometry.

10. The method of claim 1, further comprising:
(r) quantifying the optical signal(s) detected so as to thereby quantify the amount of primary protein-secondary protein interaction on the bead and comparing the quantified amount against a control curve, wherein the control curve is generated by a set of standard optically active reference beads created using said first through fourth primary agents.

11. A method of analyzing genetic pathways comprising the following steps in the recited order:
(a) providing a control and an experimental group of cells, wherein the control group of cells express at least four wild type distinct primary proteins, primary proteins A, B, C and D respectively, and wherein the experimental group of cells express variants of primary proteins A, B, C and D, wherein the variants have at least 97% or greater but less than 100% sequence identity with the primary proteins;

(b) lysing the control and the experimental group of cells;

(c) contacting each cell lysate in parallel with (i) a first primary agent attached to a surface of a magnetic bead that is not conjugated to an optically-active label, wherein the first primary agent is a binding partner capable of capturing the primary protein A or the variant of primary protein A, (ii) a second primary agent attached to a surface of a magnetic bead that is conjugated to a first primary optically-active label, wherein the second primary agent is capable of capturing the primary protein B or the variant of primary protein B, (iii) a third primary agent attached to a surface of a non-magnetic bead that is not conjugated to an optically-active label, wherein the third primary agent is capable of capturing the primary protein C or the variant of primary protein C, and (iv) a fourth primary agent attached to a surface of a non-magnetic bead that is conjugated to a second primary optically-active label, wherein the fourth primary agent is capable of capturing the primary protein D or the variant of primary protein D, wherein the second, third and fourth primary agents are different binding partners all under conditions which permit capturing of the primary agents to a primary protein-nucleic acid complex from the sample;
(d) passing the beads through a flow cytometer or optical plate reader;
(e) adjusting the forward scatter amplitude gain and side scatter voltage on a flow cytometer with a control un-complexed bead population prior to initiating the method of detecting complexed beads;
(f) detecting the optical signal of the beads, wherein each optical signal represents data from a single bead;
(g) aggregating each optical signal from each bead that have bound primary proteins A, B, C and D and variants of primary proteins A, B, C and D to identify the binding of primary proteins A, B, C and D and variants of primary proteins A, B, C and D;
(h) recovering magnetic beads complexes from the sample by applying a magnetic field and recovering non-magnetic bead complexes from the sample;
(i) contacting one or more of (i) the magnetic bead complexes not having an optically-active label; (ii) the magnetic bead complexes having a first primary optically-active label; (iii) the non-magnetic bead complexes not having an optically-active label; (iv) the non-magnetic bead complexes having a second primary optically-active label, with a Proteinase K so as to digest the proteins purified on beads and release any bound nucleic acids;
(j) sequencing nucleic acid(s) released in step (i)(i) and thereby identifying the nucleic acids that have interacted with the primary protein A; in step (i)(ii) and identifying the nucleic acids that have interacted with the primary protein B; in step (i)(iii) and identifying the nucleic acids that have interacted with the primary protein C; in step (i)(iv) and identifying the nucleic acids that have interacted with the primary protein D;
(k) comparing the primary protein-nucleic acid interactions detected from the control cell with the primary protein-nucleic acid interactions detected from the experimental cell, thereby determining whether the experimental group of cells has any functional variation in primary proteins A, B, C or D as compared to the control cell.

12. The method of claim 11, wherein recovering non-magnetic bead complexes in step (g) is achieved by centrifugation.

13. The method of claim 1, further comprising:
(r) contacting one or more of (i) the magnetic bead complexes not having an optically-active label; (ii) the magnetic bead complexes having a first primary optically-active label; (iii) the non-magnetic bead complexes not having an optically-active label; (iv) the non-magnetic bead complexes having a second primary optically-active label, with a Proteinase K so as to digest the proteins purified on beads and release any bound nucleic acids;
(s) sequencing nucleic acid(s) released in step (p)(i) and identifying the nucleic acids that have interacted with the primary protein A or the variant of primary protein A; in step (p)(ii) and identifying the nucleic acids that have interacted with the primary protein B or the variant of primary protein B; in step (p)(iii) and identifying the nucleic acids that have interacted with the primary protein C or the variant of primary protein C; and in step (p)(iv) and identifying the nucleic acids that have interacted with the primary protein D or the variant of primary protein D.

14. The method of claim 1, further comprising:
(r) contacting one or more of (i) the magnetic bead complexes not having an optically-active label; (ii) the magnetic bead complexes having a first primary optically-active label; (iii) the non-magnetic bead complexes not having an optically-active label; (iv) the non-magnetic bead complexes having a second primary optically-active label, with a Proteinase K so as to digest the proteins purified on beads and release any bound nucleic acids;
(s) amplifying nucleic acid(s) released in step (p)(i) and identifying the nucleic acids that have interacted with the primary protein A or the variant of primary protein A; in step (p)(ii) and identifying the nucleic acids that have interacted with the primary protein B or the variant of primary protein B; in step (p)(iii) and identifying the nucleic acids that have interacted with the primary protein C or the variant of primary protein C; and in step (p)(iv) and identifying the nucleic acids that have interacted with the primary protein D or the variant of primary protein D, wherein the amplifying is achieved by a method selected from the group consisting of polymerase chain reaction (PCR) and a ligation assay.

15. The method of claim 14, wherein the ligation assay is a multiplex ligation assay.

16. The method of claim 1, further comprising:
(r) contacting one or more of (i) the magnetic bead complexes not having an optically-active label; (ii) the magnetic bead complexes having a first primary optically-active label; (iii) the non-magnetic bead complexes not having an optically-active label; (iv) the non-magnetic bead complexes having a second primary optically-active label, with a Proteinase K so as to digest the proteins purified on beads and release any bound nucleic acids;
(s) contacting the nucleic acid(s) released in step (p)(i) with an optically labeled nucleic acid probe and identifying the nucleic acids that have interacted with the primary protein A or the variant of primary protein A;
contacting the nucleic acid(s) released in step (p)(ii) with an optically labeled nucleic acid probe and identifying the nucleic acids that have interacted with the primary protein B or the variant of primary protein B;
contacting the nucleic acid(s) released in step (p)(iii) with an optically labeled nucleic acid probe and identifying the nucleic acids that have interacted with the primary protein C_or the variant of primary protein C; and
contacting the nucleic acid(s) released in step (p)(iv) with an optically labeled nucleic acid probe and identifying the nucleic acids that have interacted with the primary protein D_or the variant of primary protein D.

17. The method of claim 1, further comprising:
(r) contacting one or more of (i) the magnetic bead complexes not having an optically-active label; (ii) the magnetic bead complexes having a first primary optically-active label; (iii) the non-magnetic bead complexes not having an optically-active label; (iv) the non-magnetic bead complexes having a second primary optically-active label, with a Proteinase K so as to digest the proteins purified on beads and release any bound nucleic acids; and (s) comparing the protein-nucleic interactions detected from the control cell with the protein-nucleic interactions detected from the experimental cell, thereby determining whether the experimental cell has any functional alteration caused by the variants of primary proteins A, B, C or D as compared to the control cell.

18. A method comprising the following steps in the recited order:

(a) providing experimental cells expressing at least four distinct proteins, proteins A, B, C and D respectively;

(b) fixing and permeabilizing the cells;

(c) lysing the permeabilized cells using a hypotonic salt solution, to obtain a nuclear and a whole-cell extract;

(d) contacting the nuclear and the whole-cell extract with (i) a first primary agent conjugated to a first primary optically-active label, wherein the first primary agent is a binding partner capable of capturing the protein A, (ii) a second primary agent conjugated to a second optically-active label, (iii) a third primary agent conjugated to a third optically-active label, and (iv) a fourth primary agent conjugated to a fourth primary optically-active label, wherein the second, third and fourth primary agents are different binding partners each capable of binding to the distinct proteins B, C and D, respectively;

(e) staining the whole-cell and the nuclear extract with an optically-active nuclei-staining agent;

(f) passing the whole-cell and the nuclear extract through a flow cytometer;

(g) detecting each optical signal of each nuclear and whole-cell extract, wherein each optical signal represents data from a single nucleus or single cell;

(h) determining nuclear localization of proteins A, B, C and D, wherein each optical signal from the first primary optically-active label is used to determine the nuclear localization of the protein A, each optical signal from the second primary optically-active label is used to determine the nuclear localization of the protein B, each optical signal from the third primary optically-active label is used to determine the nuclear localization of the protein C, and each optical signal from the fourth primary optically-active label is used to determine the nuclear localization of the protein D;

(i) determining cytoplasmic localization of proteins A, B, C and D, wherein each optical signal from the first primary optically-active label is used to determine the cytoplasmic localization of the protein A, each optical signal from the second primary optically-active label is used to determine the cytoplasmic localization of the protein B, each optical signal from the third primary optically-active label is used to determine the cytoplasmic localization of the protein C, and each optical signal from the fourth primary optically-active label is used to determine the cytoplasmic localization of the protein D; and (j) comparing the cytoplasmic and nuclear localizations detected from control cell with the cytoplasmic and nuclear localizations detected from the experimental cells, thereby determining whether the experimental cells has any functional variation in primary proteins A, B, C or D as compared to the control cell.

19. The method of claim 18, wherein, after step (c), nuclear extracts are enriched from the lysed cells by centrifugation and processed separately from whole-cell extract.

* * * * *